(12) United States Patent
Wang et al.

(10) Patent No.: US 7,697,658 B2
(45) Date of Patent: Apr. 13, 2010

(54) INTERIOR TOMOGRAPHY AND INSTANT TOMOGRAPHY BY RECONSTRUCTION FROM TRUNCATED LIMITED-ANGLE PROJECTION DATA

(75) Inventors: Ge Wang, Blacksburg, VA (US); Yangbo Ye, Coralville, IA (US); Hengyong Yu, Christiansburg, VA (US)

(73) Assignees: Virginia Tech Intellectual Properties, Inc., Blacksburg, VA (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 12/362,979

(22) Filed: Jan. 30, 2009

(65) Prior Publication Data

US 2009/0196393 A1 Aug. 6, 2009

Related U.S. Application Data

(60) Provisional application No. 61/025,470, filed on Feb. 1, 2008.

(51) Int. Cl.
*A61B 6/03* (2006.01)
(52) U.S. Cl. .......................................................... 378/4

(58) Field of Classification Search ...................... 378/4, 378/901; 382/131
See application file for complete search history.

(56) References Cited

U.S. PATENT DOCUMENTS 7,085,343 B2 * 8/2006 Shinno et al. .................. 378/9
2008/0056432 A1 * 3/2008 Pack et al. ..................... 378/4

OTHER PUBLICATIONS

Ye et al., A General Local Reconstruction Approach Based on a Truncated Hilbert Transform, Jun. 18, 2007, International Journal of Biomedical Imaging, Article ID 63634, 8 Pages.*

* cited by examiner

*Primary Examiner*—Edward J Glick
*Assistant Examiner*—John M Corbett
(74) *Attorney, Agent, or Firm*—Whitham, Curtis, Christofferson & Cook, P.C.

(57) ABSTRACT

A system and method for tomographic image reconstruction using truncated limited-angle projection data that allows exact interior reconstruction (interior tomography) of a region of interest (ROI) based on the linear attenuation coefficient distribution of a subregion within the ROI, thereby improving image quality while reducing radiation dosage. In addition, the method includes parallel interior tomography using multiple sources beamed at multiple angles through an ROI and that enables higher temporal resolution.

15 Claims, 15 Drawing Sheets

A

B

A

B

A

B

A

B

A

B

Global FBP    Local FBP

Local SART    Interior Recon

A

B

C

D

E

A

B

INTERIOR TOMOGRAPHY AND INSTANT TOMOGRAPHY BY RECONSTRUCTION FROM TRUNCATED LIMITED-ANGLE PROJECTION DATA

CROSS-REFERENCE TO RELATED APPLICATIONS

This application claims priority to U.S. Provisional Application Ser. No. 61/025,470 filed Feb. 1, 2008. The complete contents of that application is herein incorporated by reference.

STATEMENT OF GOVERNMENT INTEREST

This invention was made with government support under grants EB002667, EM004287 and EB007288 awarded by NIH/NIBIB. The government has certain rights in the invention.

BACKGROUND OF THE INVENTION

1. Field of the Invention

The present invention generally relates to computed tomography (CT) and, more particularly, to systems and methods for exact interior reconstruction using improved analytic continuation techniques and with the extension of such techniques to instant tomography and across other tomographic modalities.

2. Background Description

Classic CT theory targets exact reconstruction of a whole cross-section or of an entire object from complete projections, while practical applications such as medical CT, micro- and nano-CT often need to focus on a much smaller internal region of interest (ROI). Current CT theory cannot exactly reconstruct an internal ROI only from truncated projections associated with x-rays through the ROI because this interior problem does not have a unique solution. When applying traditional CT algorithms for interior reconstruction from truncated projection data, features outside the ROI may create artifacts overlapping inside features, rendering the images inaccurate or useless. Moreover, specific problems remain for pre-clinical imaging, as in the case of small animals (see Wang, G., "Micro-CT scanners for biomedical applications: an overview", *Adv. Imaging*, 2001, 16: pp. 18-27). Although there has been an explosive growth in the development of cone-beam micro-CT scanners for small animal studies, the efforts are generally limited to cross-sectional or volumetric imaging at high spatial resolution of 20-100 µm at large radiation dose.

Traditional CT is necessarily associated with x-ray source and/or detector scanning so that projections can be collected from a sufficient number of orientations. Although the multi-source strategy has been a natural solution to higher temporal resolution CT and already used in the classic Mayo Clinic Dynamic Spatial Reconstructor (see Robb, R. A., et al, *High-speed three-dimensional x-ray computed tomography: The dynamic spatial reconstructor. Proceedings of the IEEE*, 1983. 71(3): p. 308-319, and Ritman, E. L., R. A. Robb, and L. D. Harris, *Imaging physiological functions: experience with the DSR*. 1985: *philadelphia: praeger*), the modern Siemens dual-source cone-beam scanner (see Flohr, T. G., et al, *First performance evaluation of a dual-source CT (DSCT) system. European Radiology*, 2006. 16(2): p. 256-268), and other systems, such an x-ray scanning mechanism remains indispensible. The bulkiness of sources/detectors in limited physical space has previously made it impossible to collect simultaneously a sufficient number of projections simultaneously.

The importance of performing exact image reconstruction from the minimum amount of data has been recognized since the introduction of CT scanning. A recent milestone was the two-step Hilbert transform method (see Noo et al. "A two-step Hilbert transform method for 2D image reconstruction". *Physics in Medicine and Biology*, 2004. 49(17): p. 3903-3923), which was further expanded by Defrise et al. "Truncated Hilbert transform and image reconstruction from limited tomographic data." *Inverse Problems*, 2006. 22(3): p. 1037-1053.

Despite the impressive advancement of the CT technology, there are still unmet, critical and immediate needs such as those mentioned above for better image quality at lower doses in many biomedical and other investigations.

SUMMARY OF THE INVENTION

An exemplary object is to provide a new method and system for providing interior tomography.

Another exemplary object is to provide a system and method for exact interior reconstruction is performed using truncated limited-angle projection data.

Still another exemplary object is to provide instant tomography where a ROI or VOI is provided without moving an X-ray source on a path around a patient. For purposes of this description the ROI will be understood to include VOI, and vice versa.

According to one exemplary embodiment, the interior problem can be solved in a theoretically exact and numerically stable fashion if a small sub-region within an ROI is known. The reconstruction schemes only use projection data associated with lines through a ROI or volume of interest (VOI) to be reconstructed, and are referred to as interior tomography, in contrast with traditional CT reconstruction, which does not allow two-side data truncation. Interior tomography enables faithful resolution of features anywhere inside an ROI using data collected along x-ray beams probing the ROI with knowledge of a sub-region (i.e., the linear attenuation coefficient function on the sub-region) of non-zero measure in the ROI. Exact knowledge of a sub-region can often be assumed because in many cases the x-ray linear attenuation coefficients of air gaps or voids, water, blood or other liquid, or other calibrated structures such as implants is known; more generally, a pre-scan (even in lower resolution) can be used to provide such prior knowledge. Other forms of knowledge may be also included and used along with the interior reconstruction such as low-resolution images of the ROI to be reconstructed.

According to another exemplary embodiment, novel cone-beam techniques are developed which permit higher spatial contrast and temporal resolution at less radiation dose. That is, superior dynamic volumetric imaging is attained while minimizing the radiation dosage and imaging time, making it safer for patients and enabling more images to be taken without compromising safety. Systems and methods use interior tomography to provide instantaneous temporal resolution of a small ROI without the need to move an x-ray source on a trajectory around a patient, producing a "snapshot", herein referred to as ultrafast or instant tomography. In addition, the user can easily move to another region of interest or "roam" to re-position or enlarge such a snapshot, revolutionizing the CT imaging paradigm. This reduced time for imaging will enrich diagnostic information with improved temporal resolution, and result in increased numbers of screening procedures that can be performed on an individual scanning apparatus providing addition benefits of reduced requirements for data storage and cost savings.

BRIEF DESCRIPTION OF THE DRAWINGS

The foregoing and other objects, aspects and advantages will be better understood from the following detailed description of a preferred embodiment of the invention with reference to the drawings, in which:

FIG. 1A shows conventional tomography allows exact reconstruction of an object from a half-scan where every point of the object is irradiated with x-rays from all directions. FIG. 1B shows that it was proved impossible to reconstruct uniquely an ROI if only the ROI is irradiated from all the directions (the interior problem). FIG. 1C shows systems and methods we developed previously where the interior problem can be exactly and stably solved assuming a known sub-region of the ROI using truncated Hilbert Transform data (Ye, Y., et al., A General Local Reconstruction Approach Based on a Truncated Hilbert Transform. International Journal of Biomedical Imaging, 2007, Article ID: 63634, 8 pages)

FIG. 13A shows the global filtered back projection (FBP) reconstruction containing an ROI bounded by a circle imposed on each image. FIG. 13B shows a magnification of the ROI. FIG. 13C shows the local FBP after smooth data extrapolation. FIG. 13D shows the local simultaneous algebraic reconstructive technique (SART) with ordered subsets. FIG. 13E shows local reconstruction via interior tomography. FIGS. 13F and 13G are profiles along the horizontal and vertical lines within the FIGS. 13B-13E. The display window is [−800HU, 700HU].

DETAILED DESCRIPTION

Section I

Interior Tomography with Prior Knowledge

Interior tomography becomes possible if one knows the object function $f(x)$ in a sub-region. The algorithms use the following mathematical techniques. The first is a formula proved by Gel'fand-Graev (see Gelfand, I. M. and M. I. Graev, *Crofton Function And Inversion Formulas In Real Integral Geometry*. Functional Analysis And Its Applications, 1991. 25(1): p. 1-5) which was later rediscovered by Pack- Noo-Clackdoyle (see Pack, J. D., F. Noo, and R. Clackdoyle, *Cone-beam reconstruction using the backprojection of locally filtered projections*. IEEE Transactions on Medical Imaging, 2005. 24(1): p. 70-85).

Theorem I-(Gel'fand-Graev 1991)

The filtered data $PV \int_0^{2\pi} \frac{\partial}{\partial q} D_f(y(q), \theta(s, x, \gamma))\Big|_{q=s} \frac{d\gamma}{\sin\gamma}$ can be expressed as a Hilbert transform.

In the 1D setting, the Hilbert transform can be written as $$g(y) = \frac{1}{\pi} PV \int_{c_1}^{c_2} \frac{f(x)dx}{y-x} = (H_L f)(y), \quad (3.\text{I-1})$$

if $f(x)$ is supported on $[c_1, c_2]$. Note that the PV integral here becomes an ordinary integral if $y \notin [c_1, c_2]$. Because $f(x)$ is continuous, (I-1) actually defines a single-valued analytic function for complex variable $y \notin [c_1, c_2]$. The next method we will need is an inversion formula for truncated Hilbert transform.

Theorem I-2 (Tricomi 1951)

$f(x)$ can be recovered by                                    (3.I-2)

$$\sqrt{1-x^2} f(x) = C_f + \frac{1}{\pi} PV \int_{-1}^{1} g(y)\sqrt{1-y^2} \frac{dy}{y-x},$$

$$C_f = \frac{1}{\pi} \int_{-1}^{1} f(x)dx.$$

(see Tricomi, F. G., *On the finite Hilbert Transform* Quarterly Journal of Mathematics 1951. 2(1); p. 199-211) (Here we set $c_1 = -1$ and $c_2 = 1$ for simplicity.)

Figure 2:
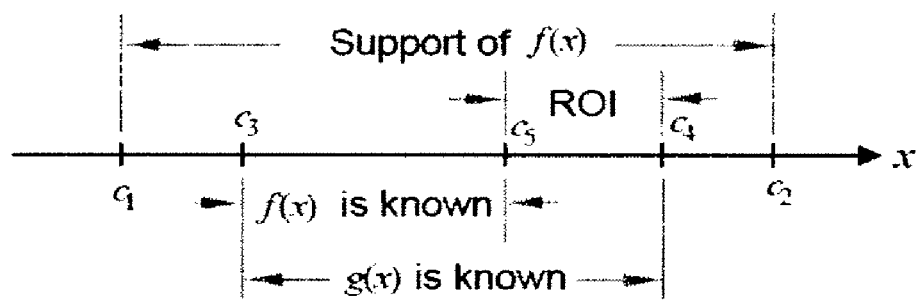
FIG. 2 is a diagrammatic illustration of a one-dimensional (1D) setting for interior reconstruction of a region of interest (ROI) with prior knowledge of a landmark.

Assume that $g(x)$ is measured on $[c_3, c_4]$, unknown on $[c_1, c_3]$ and $[c_4, c_2]$, and $f(x)$ is known on $[c_3, c_5]$, where with $c_1 < c_3 < c_5 < c_4 < c_2$ (see FIG. 2). $c_1 = -1$ $c_2 = 1$ The function $$h(z) = \frac{1}{\pi} PV \int_{c_1}^{c_3} g(y)\sqrt{1-y^2} \frac{dy}{y-z} + \frac{1}{\pi} PV \int_{c_4}^{c_2} g(y)\sqrt{1-y^2} \frac{dy}{y-z} \quad (3.\text{I-3})$$

cannot be evaluated because $g(x)$ is unknown on $[c_1, c_2]$ and $[c_4, c_2]$. Its nth derivative is $$h^{(n)}(z) = \frac{1}{\pi} \int_{c_1}^{c_3} g(y)\sqrt{1-y^2} \frac{n!dy}{(y-z)^{n+1}} + \frac{1}{\pi} \int_{c_4}^{c_2} g(y)\sqrt{1-y^2} \frac{n!dy}{(y-z)^{n+1}}.$$

Consequently, $h(x)$ is analytic on $\mathbb{C}$ with cuts along $[c_1, c_2]$ and $[c_4, c_2]$. By Tricomi's Theorem I-2,                                                  (3.I-4)

-continued $$\sqrt{1-z^2} f(z) = C_f + \frac{1}{\pi} PV \int_{c_3}^{c_4} g(y)\sqrt{1-y^2} \frac{dy}{y-z} + h(z).$$

Thus $h(x)$ is known on $[c_3, c_5]$, because $f(x)$ is known on $[c_3, c_5]$ and $g'(x)$ is known on $[c_2, c_4]$.

Now we need the third technique: An analytic function $h(z)$ is uniquely determined by its values on $[c_2, c_4]$. Analytic continuation of $h(z)$ from $[c_2, c_5]$ to $[c_5, c_4]$ will reconstruct $f(x)$ on $[c_5, c_4]$ by (I-5) below.

Theorem I-3 (Ye-Yu-Wei-Wang 2007) Let $-1 = c_1 < c_2 < c_5 < c_4 < c_2 = 1$. Suppose that $f(x)$ is smooth of compact support on $[-1, 1]$, $f(x)$ is known on $[c_2, c_5]$, $g(x)$ as in (I-1) is known on $[c_3, c_4]$ and $C_f$ as in (I-2) is known (FIG. 2). Then $f(x)$ can be uniquely reconstructed on $[c_5, c_4]$ by $$\sqrt{1-x^2} f(x) = C_f + \frac{1}{\pi} PV \int_{c_3}^{c_4} g(y)\sqrt{1-y^2} \frac{dy}{y-x} + h(x) \quad (3.\text{I-5})$$

using analytic continuation of $h(z)$ as defined in (I-3) from $[c_3, c_5]$ to $[c_5, c_4]$.

This analytic continuation method was first used by Defrise-Noo-Clackdoyle-Kudo (see Defrise, M., et al., *Truncated Hilbert transform and image reconstruction from limited tomographic data*. Inverse Problems, 2006. 22(3): p. 1037-1053), to extend earlier results on limited-data reconstruction by Noo-Clackdoyle-Pack (see Noo, F., R. Clackdoyle, and J. D. Pack, *A two-step Hilbert transform method for 2D image reconstruction*. Physics in Medicine and Biology, 2004. 49(17): p. 3903-3923). Similar results were announced by Kudo (see Kudo, H. *Analytical image reconstruction methods for medical tomography—Recent advances and a new uniqueness result*, in Mathematical Aspects of Image Processing and Computer Vision 2006), also proved independently by Kudo-Courdurier-Noo-Defrise (see Kudo, H., et al., *Tiny a priori knowledge solves the interior problem in computed tomography*. Phys. Med. Biol., 2008. 53(9): p. 2207-2231) and Courdurier-Noo-Defrise-Kudo (see Courdurier, M., et al., *Solving the interior problem of computed tomography using a priori knowledge*. Inverse Problems, 2008. 24: p. Article ID 065001, 27 pages).

Figure 3:
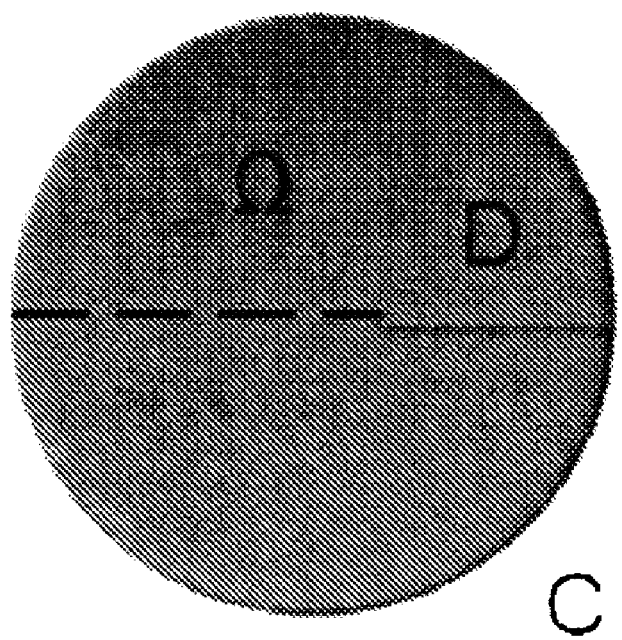
FIG. 3 is a diagram showing Region $\Omega$ bounded by a circle C and a cut D.

As in Defrise-Noo-Clackdoyle-Kudo (Defrise, M., et al., *Truncated Hilbert transform and image reconstruction from limited tomographic data*. Inverse Problems, 2006. 22(3): p. 1037-1053), the stability of the interior reconstruction above can be proved using Nevanlinna's principle. To see use this principle, consider the region $\Omega$ bounded by a circle C and a cut D, as in FIG. 3. Assume that an analytic function $f(z)$ in $\Omega$ is bounded on the boundary: $|f(z)| \leq M$ on C, $|f(z)| \leq \epsilon$ on D, for a positive constant M and an arbitrarily small positive $\epsilon$. The goal is to get a bound for $f(z)$ on the dotted line segment.

Theorem I-4 (Nevanlinna's principle) Under the above setting, there is a harmonic function $\omega(z)$ on $\Omega$ such that $\omega|_D = 0$, $\omega|_C = 1$ and $$|f(z)| \leq M(\epsilon/M)^{1-\omega(z)}$$

for all z in $\Omega$.

Therefore on the dotted line segment, the bound for $f(z)$ is close to $\epsilon$ at the end next to D but becomes a small fractional power of $\epsilon$ toward the other end. This is the same situation as the 1D interior tomography with prior knowledge. In FIG. 2, on the ROI $[c_5,c_4]$, the error bound for reconstructed $f(z)$ is close to $\epsilon$ at the end $c_5$, but becomes a small fractional power of $\epsilon$ toward $c_4$, where $\epsilon>0$ is a bound for measurement error.

Section II

SVD Method with or without Chord Averaging

Figure 1:
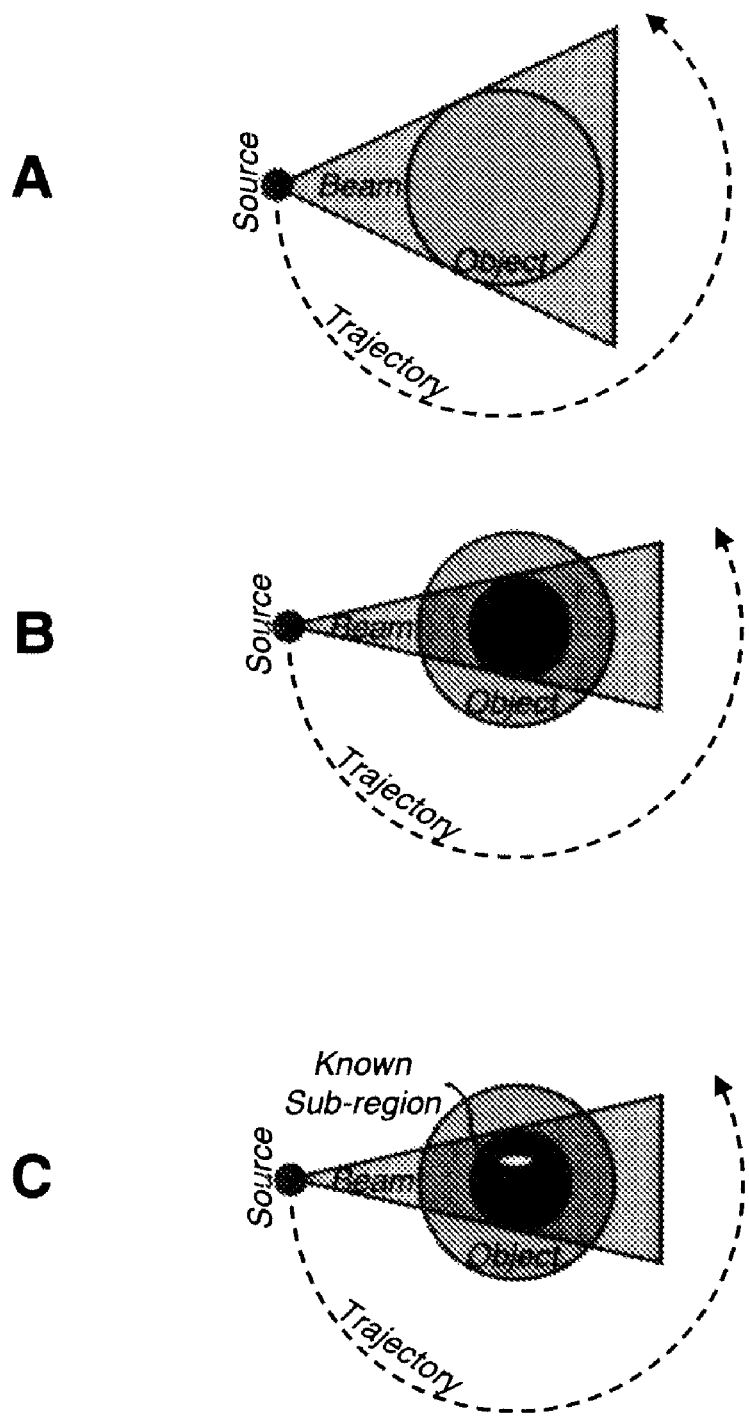
FIGS. 1A to 1C are diagrams illustrating the interior tomography concept solving the interior problem.

We previously demonstrated the ability to solve the problem of interior tomography using a projection-onto-convex-sets (POCS) method (see FIG. 1) (Ye, Y., et al., A General Local Reconstruction Approach Based on a Truncated Hilbert Transform. International Journal of Biomedical imaging, 2007. 2007: p. Article ID: 63634, 8 pages). We subsequently developed a singular value decomposition (SVD) methodology for interior tomography that is computationally superior to the POCS method and provides a comparable image quality (Hengyong Yu, Yangbo Ye and Ge Wang; Interior reconstruction using truncated Hilbert transform via singular value decomposition; Journal of X-ray Science and Technology, 16(4):243-251, 2008).

Now, let us describe a SVD method coupled with the chord averaging technique that retains the advantage of computational superiority over POCS while reducing noise compared to the prior SVD methodology.

In practice, the 1D function $g(y)$ can be obtained on a generalized PI-line/chord by backprojecting the weighted differential projection data. Once $g(y)$ is known on $(c_3,c_4)$, $f(x)$ can be recovered. We adapted a projection-onto-convex-sets (POCS) method to reconstruct 1D $f(x)$ iteratively from truncated data $g(y)$ and produced promising numerical results (see Ye, Y., et al., *A General Local Reconstruction Approach Based on a Truncated Hilbert Transform*. International Journal of Biomedical Imaging, 2007, Article ID: 63634, 8 pages) but it was computationally very expensive and sensitive to noise.

On a discrete grid, $g(y)$ is sampled along a chord through the known sub-region $(c_3,c_5)$ in the ROI as $B=[b_1,b_2,\ldots,b_P]^T$, and $f(x)$ on the chord as $A=[a_1,a_2,\ldots a_Q]^T$. Then, the Hilbert transform is represented as $B=HA$, where H is a coefficient matrix corresponding to the Hilbert transform kernel. Because A is partially known, A can be divided into the known and unknown parts $A_k$ and $A_u$. Accordingly, H is divided into $H_k$ and $H_u$. Hence, $\overline{B}=B-H_kA_k=H_uA_u$, which represents a linear inversion problem. Because all the rows of $H_u$ are formed by the truncated discrete Hilbert transform kernel, one can utilize the properties of $H_u$ to solve the unknown $A_u$ from the known $\overline{B}$. The unknown $A_u$ includes two parts: the part $A_{ue}$ within the ROI to be exactly reconstructed and the part $A_{un}$ outside the ROI which cannot be exactly recovered. The goal is to ensure that $A_{ue}$ is reconstructed as precisely and robustly as possible. Without loss of generality, a regularization scheme can be expressed as $$\hat{A}_u = \underset{A_u}{\mathrm{argmin}}(\|\overline{B} - H_u A_u\|^2 + \xi^2\|LA_u\|^2), \quad (\text{II-1})$$

where L and $\xi$ are a regularization constraint and a relaxation coefficient respectively. Our initial SVD solution is to implement the so-called Tikhonov regularization with a unit diagonal constraint matrix L. The SVD method is a closed-form solution to interior tomography. Our experiments show that the SVD method is >200 times faster and produces comparable image quality relative to the POCS method (7 minutes versus 1,500 minutes).

To suppress image noise, the reconstruction at a particular point is obtained by averaging the results at that point through different chords. Thus, we call our methodology a singular-value-decomposition and chord-averaging approach for interior tomography. This seemly simple method actually allows us to transfer the reconstruction strategy from a 1D based scheme to a setting of higher dimensions. While the above description is based on measured the truncated Hilbert transform, similar procedures can be formulated based on measured differences of two Hilbert transforms, which is described below (Ye Y et al., "Exact interior reconstruction from truncated limited-angle projection data", International Journal of Biomedical Imaging 2008: 2008:427989; Yangbo Ye, Hengyng Yu and Ge Wang, Interior Tomography: Mathematical Analysis, to appear in special volume "Biomedical Mathematics: Promising Directions in Imaging, Therapy Planning and Inverse Problems" (Editors: Yair Censor, Ming Jiang and Ge Wang), Proceedings of Huangguoshu International Interdisciplinary Conference on Biomedical Mathematics on Nov. 6, 2008).

Section III

Partial Limited-Angle Interior Tomography

Figure 4:
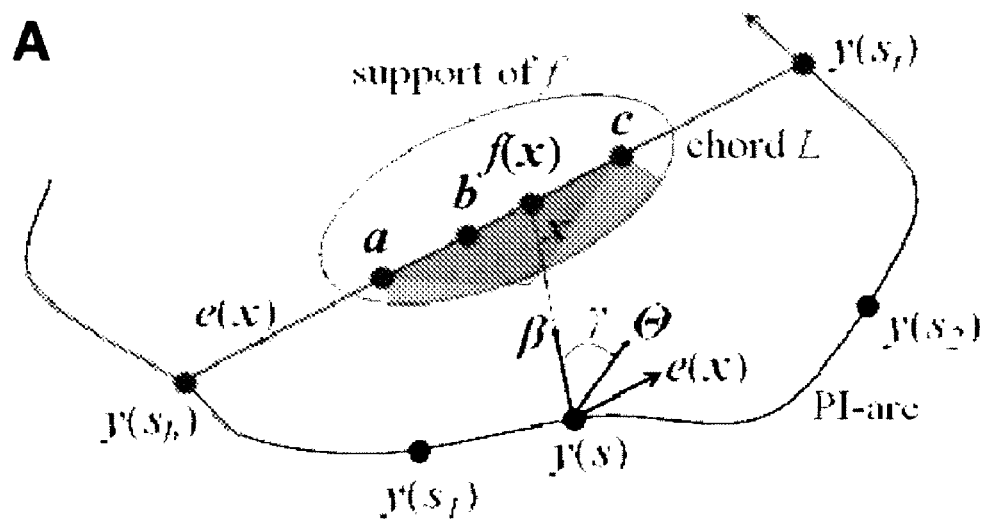
FIGS. 4A and 4B are diagrammatic illustrations of 1D and two-dimensional (2D) interior tomography with truncated limited-angle projections on a ROI.
Figure 4:
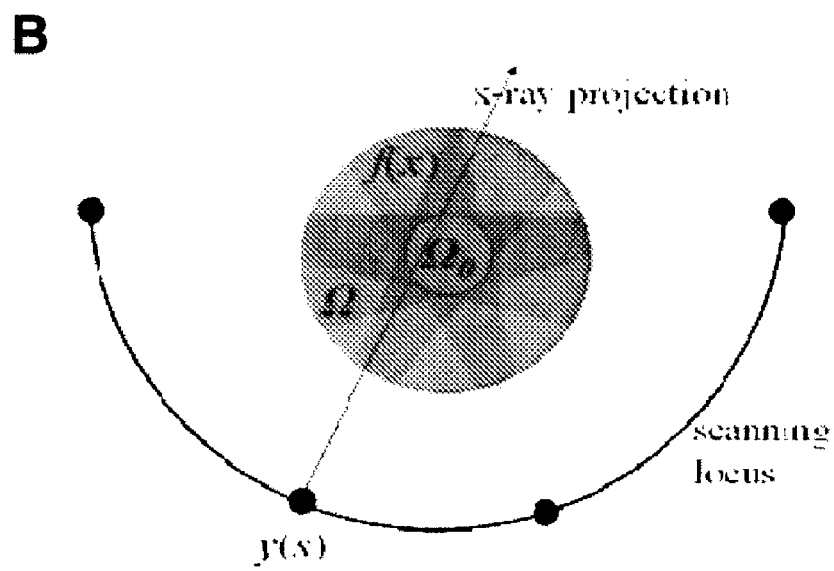

Assume that there are three points a, b and c on a chord L from $y(s_b)$ to $y(s_t)$ as in FIG. 4(*a*). Assume that $f(x)$ is known on L between a and b. Suppose that the projection data are known for any $s\in[s_b,s_t]$ and any $x\in L$ between a and b. Also suppose that the projection data are known for any $s\in[s_1, s_2]$ and for any $x\in L$ between b and c. In other words, we have 180° projections on the region where $f(x)$ is known but only limited-angle projections on the ROI. Since the segment of L between a and c may be contained in the support of $f(x)$, this is an interior tomography problem with truncated limited-angle projections. Our goal is to reconstruct $f(x)$ on L between b and c.

Theorem III-1 (Ye-Yu-Wang 2008) With the setting as above as in FIG. 4(*a*), $f(x)$ can be uniquely reconstructed on L between b and c.

The setting of this problem can be easily generalized to 2D and 3D. In the 2D setting as in FIG. 4(*b*), x-ray projections can be focused on the subregion $\Omega_a$ where $f(x)$ is known. Our algorithm can be applied to reconstruct $f(x)$ uniquely in a neighborhood $\Omega$ of $\Omega_a$.

A new technique used in the proof of Theorem III-1 is the integral of Cauchy's type $$H(z) = PV \int_a^b \frac{g(y)}{y-z} dy. \quad (4.\text{III-1})$$

Here for $H(z)$ for $z\in[a, b]$ given by the Cauchy principal value of the integral in (III-1), while on $\mathbb{C}$ with a cut on [a, b] the integral is an ordinary integral. Hence $H(z)$ is a single-valued analytic function on $\mathbb{C}$ with a cut on [a, b].

Theorem III-2 (The Plemelj-Sokhotski formula) Let $f(z)$ be defined as in (III-1) for any $z\in\mathbb{C}$. Then for any $x\in[a, b]$, we have $$H(x) = \frac{1}{2} \lim_{\substack{z \to x \\ Imz > 0}} H(z) + \frac{1}{2} \lim_{\substack{z \to x \\ Imz < 0}} H(z). \quad (4.\text{III-2})$$

We remark that because (III-2) is used in the proof of Theorem III-1, Nevanlinna's principle cannot be used to prove stability of the reconstruction in Theorem III-1. In fact, (III-2) gives us values of the PV integral in (III-1) using the behavior of the analytic function $f(z)$ approaching to its boundary [a, b]. This is a different situation to FIG. 3 where the dotted line segment is inside the region of holomorphy.

The limit formula (III-2) can also be used to extend the results in Theorem I-3. In fact, from the discussion above, we know that the function h(z) is a single-valued analytic function on ℂ with cuts along $[c_1, c_2]$ and $[c_4, c_2]$ and is uniquely determined by its values on $[c_2, c_4]$. By Theorem III-2, for any x in $[c_1, c_2]$ and $[c_4, c_2]$, $$h(x) = \frac{1}{2} \lim_{\substack{z \to x \\ Im\, z > 0}} h(z) + \frac{1}{2} \lim_{\substack{z \to x \\ Im\, z < 0}} h(z). \quad (4.\text{III-3})$$

Therefore h(x) is known on $[c_1, c_2]$ and $[c_4, c_2]$ by (III-3). Substituting these known values of h(x) on $[c_1, c_2]$ and $[c_4, c_2]$ into (I-5), we can now uniquely reconstruct $f(x)$ on $[c_1, c_2]$ and $[c_4, c_2]$ because $C_f$ and the PV integral in (I-5) are known for any x. This result is summarized in the following theorem.

Theorem III-3 Let $-1 = c_1 < c_2 < c_5 < c_4 < c_2 = 1$. Suppose that $f(x)$ is smooth of compact support on $[-1, 1]$, $f(x)$ is known on $[c_2, c_5]$, g(x) as in (I-1) is known on $[c_2, c_4]$, and $C_f$ as in (I-2) is known (FIG. 2). Then $f(x)$ can be uniquely reconstructed on the whole support $[-1, 1]$ by (I-5) using analytic continuation of h(z) as defined in (I-3) from $[c_2, c_5]$ to $[c_5, c_4]$ and by the limit formula (III-3) to $[c_1, c_2]$ and $[c_4, c_2]$.

The setting in FIG. 2 for Theorems I-3 and III-3 is only a simplified illustration of the applicable general case. For instance, these theorems can be trivially extended to the case when there is an interval between the ROI and the interval on which $f(x)$ is known.

Figure 5:
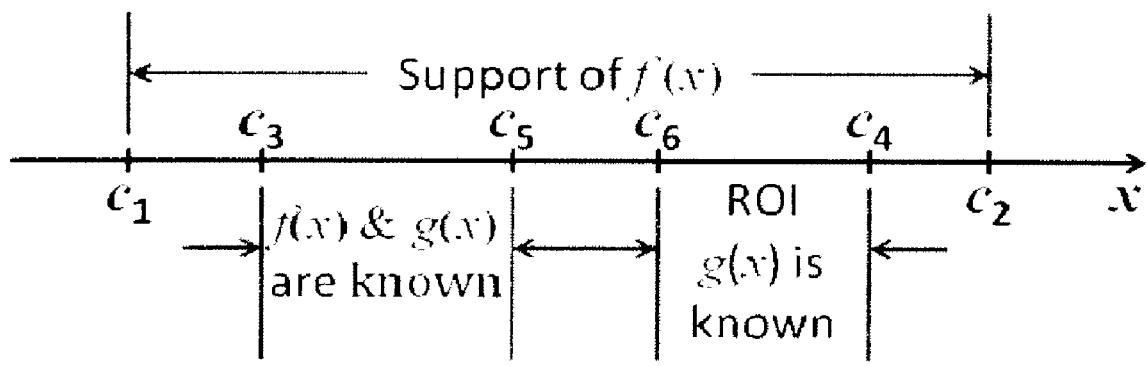
FIG. 5 is a diagrammatic illustration of 1D interior tomography of a ROI with prior knowledge of a landmark.

Theorem III-4 Let $-1 = c_1 < c_2 < c_5 < c_6 < c_4 < c_2 = 1$. Suppose that $f(x)$ is smooth of compact support on $[-1, 1]$, $f(x)$ is known on $[c_2, c_5]$, g(x) as in (I-1) is known on $[c_2, c_5]$ and $[c_6, c_4]$ and $C_f$ as defined in (I-2) is known (FIG. 5). Then $f(x)$ can be uniquely reconstructed on the whole support $[-1, 1]$ by (I-5) using analytic continuation of h(z) as defined in (I-3) from $[c_2, c_5]$ to $[c_6, c_4]$ and by the limit formula (III-3) to $[c_1, c_2]$, $[c_5, c_6]$ and $[c_4, c_2]$.

To perform the limited angle interior reconstruction, we can use a POCS scheme using truncated data through an ROI. For that purpose, the reconstruction can utilize the following constraints for the convex set: (1) projections and associated Hilbert transform data and/or differences of two Hilbert transforms; (2) known prior information; (3) non-negativity.

Figure 6:
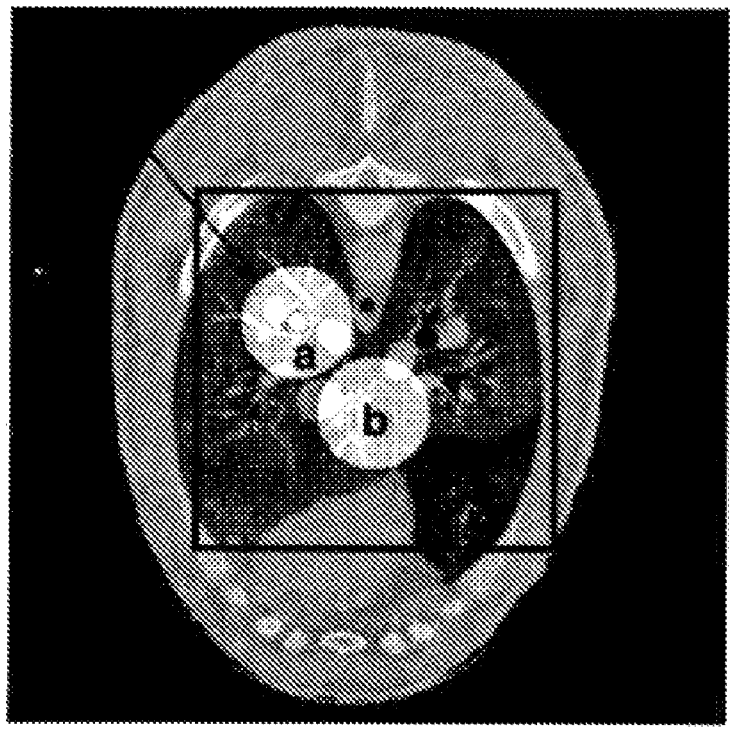
FIG. 6 is an example to demonstrate the interior reconstruction using the configuration of FIG. 5. 6A is a reconstruction from a complete dataset, where around the known trachea we specific two regions A and B. 6B is the local interior reconstruction only using the truncated data through regions A or B.
Figure 6:
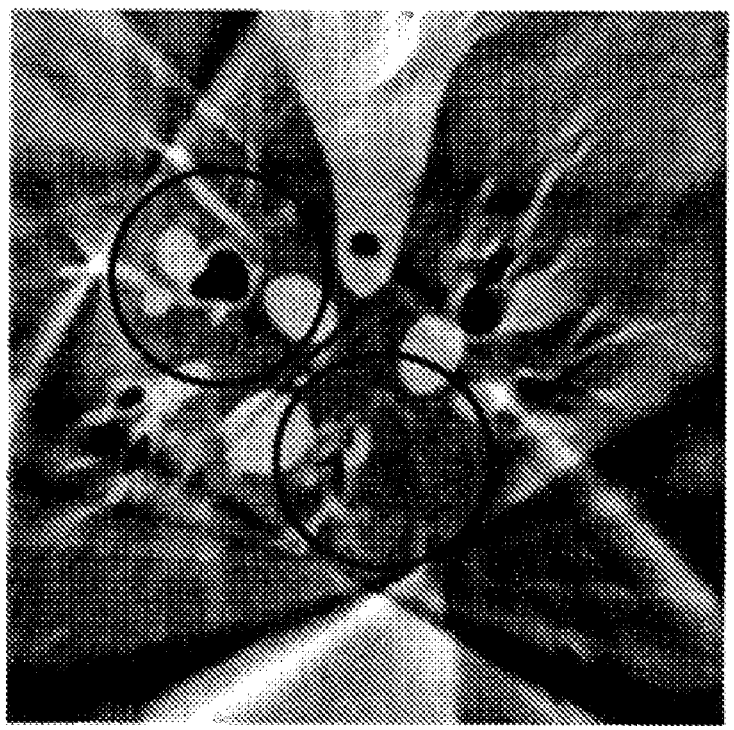

To demonstrate the feasibility of our algorithm, we performed a simulation based on the CT experiment with a living sheep, which was approved by Virginia Tech IACUC committee (exempt review). The chest of a sheep was scanned in fan-beam geometry on a SIEMENS 64-Slice CT scanner (100 kVp, 150 mAs). The radius of the x-ray source trajectory was 570 mm. There were 1160 projections uniformly collected over a 360° range, and 672 detectors were equi-angularly distributed per projection. The radius of the field of view (FOV) was 250.5 mm. First, an entire 290.56 mm by 290.56 mm cross-section was reconstructed into 1024×1024 pixels using the popular FBP method from complete projections. Second, a trachea in which we already knew the CT number of the internal air was selected in reference to the reconstructed image. Around the trachea, we specified a circular ROI A of radius 80 pixels and kept only the projection data through the ROI. Meanwhile, we specified another circular ROI B of radius 80 which does not interact with ROI A and keep the projection data trough ROI B too. The results are shown in FIG. 6.

Section IV

Limited-Angle Interior Tomography

Theorem III-1 is not a truly limited-angle reconstruction, because the line segment $\overline{ab}$ in FIG. 4(a) and subregion $\Omega_o$ need x-ray projections covering 180°. In this section, we report a new result on limited-angle tomography. First we need Gel'fand-Graev's formula (see Gelfand, I. M. and M. I. Graev, *Crofton Function And Inversion Formulas In Real Integral Geometry*. Functional Analysis And Its Applications, 1991. 25(1): p. 1-5), which was rediscovered by Pack-Noo-Clackdoyle (see Pack, J. D., F. Noo, and R. Clackdoyle, *Cone-beam reconstruction using the backprojection of locally filtered projections*. IEEE Transactions on Medical Imaging, 2005. 24(1): p. 70-85).

Figure 7:
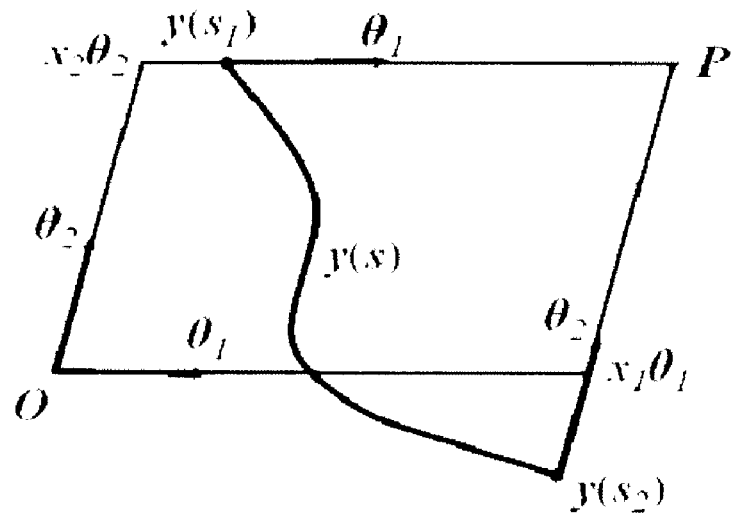
FIG. 7 is diagram showing that limited-angle scanning of P from $y(s_1)$ to $y(s_2)$ along the curve y(s) points on the plane can be written as $P'=x'_1\theta_1+x'_2\theta_2$.

Theorem IV-1 (Gel'fand-Graev's formula) Let y(s), $s_1 \leq s \leq s_2$, be a smooth scanning curve, P a point, and $\theta_i$ be the unit vector from $y(s_i)$ to P (FIG. 7). Then $$\int_{s_1}^{s_2} \frac{d}{dh} D_f(s, P - y(s) + hy'(s)) \bigg|_{h=0} ds + \quad (5.\text{IV-1})$$

$$D_f(s_2, P - y(s_2)) - D_f(s_1, P - y(s_1)) =$$

$$\frac{1}{\pi} PV \int_{\mathcal{R}} \frac{f(P - t\theta_2)}{t} dt - \frac{1}{\pi} PV \int_{\mathcal{R}} \frac{f(P - t\theta_1)}{t} dt.$$

When $\theta_1 = -\theta_2$, the two integrals on the right side of (IV-1) can be combined into one integral and the last two terms on the left side of (IV-1) cancel each other. The resulting formula $$\int_{s_1}^{s_2} \frac{d}{dh} D_f(s, P - y(s) + hy'(s)) \bigg|_{h=0} ds = \quad (5.\text{IV-2})$$

$$\frac{2}{\pi} PV \int_{\mathcal{R}} \frac{f(P - t\theta_2)}{t} dt$$

is indeed Theorem I-1. (IV-2) is the way how Gel'fand-Graev and Park-Noo-Clackdoyle applied (IV-1) to reconstruction problems. Note that the line segments from $y(s_1)$ to P and from $y(s_2)$ to P become a single chord when $\theta_1 = -\theta_2$.

Figure 8:
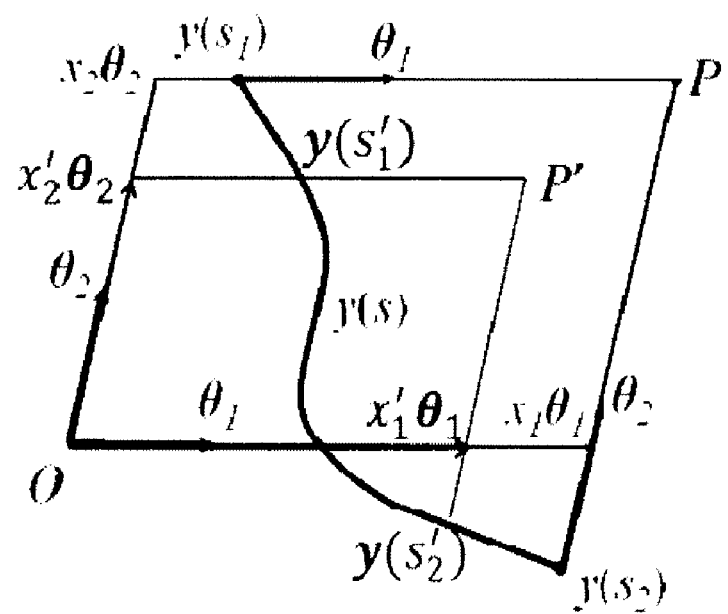
FIG. 8 is a diagram illustrating limited-angle scanning of P' from $y'(s_1)$ to $y'(s_2)$ along the curve y(s).

What we do is to use (IV-1) without setting $\theta_1 = -\theta_2$. To this end, let us reformulate the setting in FIG. 7. We assume that the curve y(s), $s_1 \leq s \leq s_2$, is a planar curve. Since $\theta_1$ and $\theta_2$ span the plane, the point P can be written as $P = x_1 \theta_1 + x_2 \theta_2$. Similarly, other points on the plane can be written as $P' = x'_1 \theta_1 + x'_2 \theta_2$ (FIG. 8). In FIG. 7, $y(s\!\!\downarrow\!\!1)$, $y(s\!\!\downarrow\!\!2)$ and P determine a plane, while the curve y(s) may be a curve in the 3D space. Here, we will only consider the 2D case by assuming that y(s) is a planar curve and P is on the plane determined by y(s). The vectors $\theta_1$, $\theta_2$ form a basis of $R^2$ so that we can write $P=x_1\theta_1+x_2\theta_2$ uniquely (FIG. 7). Then the right side of (IV-1) can be written as $$\frac{1}{\pi}PV\int_{\mathcal{R}}\frac{f(x_1\theta_1+x_2\theta_2-t\theta_2)}{t}dt - \qquad (5.\text{IV-3})$$

$$\frac{1}{\pi}PV\int_{\mathcal{R}}\frac{f(x_1\theta_1+x_2\theta_2-t\theta_1)}{t}dt =$$

$$\frac{1}{\pi}PV\int_{\mathcal{R}}\frac{f(x_1\theta_1-t\theta_2)}{t+x_2}dt - \frac{1}{\pi}PV\int_{\mathcal{R}}\frac{f(x_2\theta_2-t\theta_1)}{t+x_1}dt$$

According to (IV-1), (IV-3) can be computed from projections along y(s). Fix $\theta_1$, $\theta_2$. Then $$\frac{1}{\pi}PV\int_{\mathcal{R}}\frac{f(x_1'\theta_1-t\theta_2)}{t+x_2'}dt - \frac{1}{\pi}PV\int_{\mathcal{R}}\frac{f(x_2'\theta_2-t\theta_1)}{t+x_1'}dt \qquad (5.\text{IV-4})$$

can be measured for any $x'_1$ and $x'_2$ such that $P'=x'_1\theta_1+x'_2\theta_2$ is inside the region in FIG. 8. In fact, (IV-4) can be obtained from projections from y(s'$_1$) to y(s'$_2$) in FIG. 8. Note that in (IV-4), the first term is a Hilbert transform in $x'_2$, while the second term is a Hilbert transform in $x'_1$. Those two terms are integrals of Cauchy's type, and hence define two analytic functions of $x'_2 \in C$ and $x'_1 \in C$, respectively. This observation may lead to various reconstruction strategies.

Figure 9:
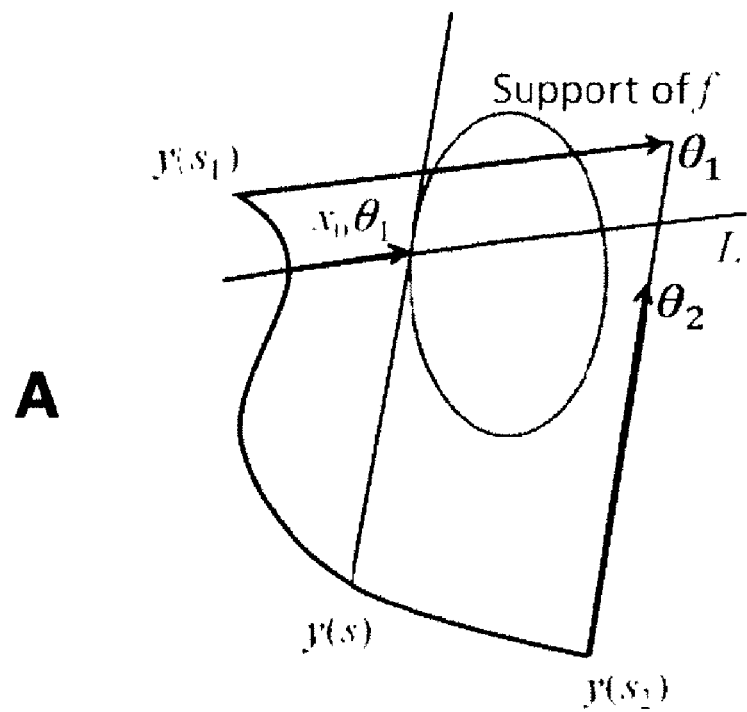
FIGS. 9A and 9B are diagrammatic illustrations of limited-angle tomography showing setting that allows measurement of (9A) $C_f(x'_2)$ from −1 to 1 and (9B) $C_f(x'_2)$ under a rescaling of Tricomi's truncated Hilbert inversion formula.
Figure 9:
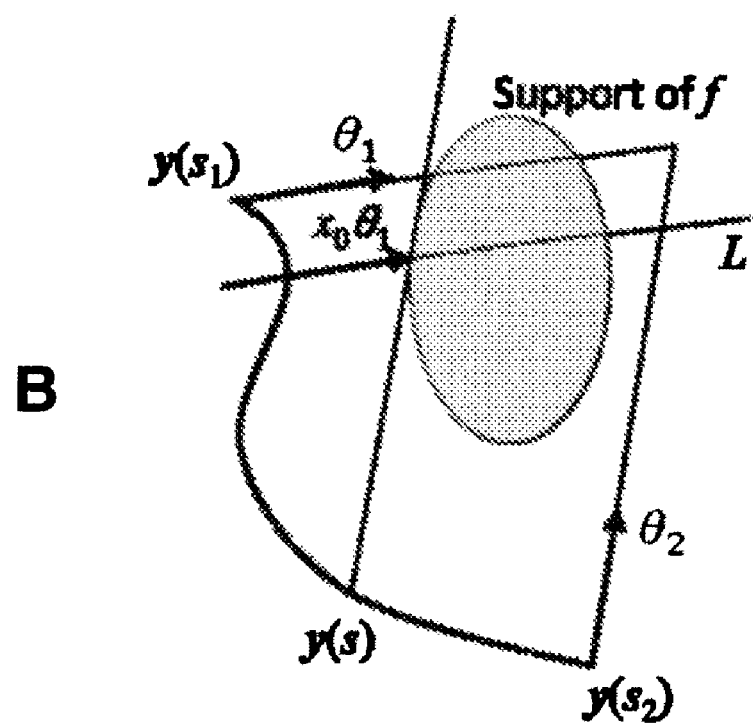

As one example, let us consider the settings in FIG. 9. We can find $x_0$ such that whenever $x'_1 \leq x_0$, $f(x'_1\theta_1-t\theta_2)=0$ for any t. Therefore the first term in (IV-4) vanishes for $x'_2$ when $x'_1 \leq x_0$, and hence $$-\frac{1}{\pi}PV\int_{\mathcal{R}}\frac{f(x_2'\theta_2-t\theta_1)}{t+x_1'}dt = -\frac{1}{\pi}PV\int_{\mathcal{R}}\frac{f(x_2'\theta_2-t\theta_1)}{x_1'-t}dt \qquad (5.\text{IV-5})$$

$$= g_{\theta_1\theta_2}(x_1', x_2')$$

is known for $x'_2$ when $x'_1 \leq x_0$.

Applying Tricomi's truncated Hilbert inversion formula (I-2) to (IV-5) along the line L in the $\theta_1$ direction, we can express $f(x'_1\theta_1+x'_2\theta_2)$ after suitable rescaling:

$$\sqrt{1-x_1'^2}\,f(x_1'\theta_1+x_2'\theta_2) = \qquad (5.\text{IV-6})$$

$$C_f(x_2') + \frac{1}{\pi}PV\int_{-1}^{1}g_{\theta_1\theta_2}(y, x_2')\sqrt{1-y^2}\,\frac{dy}{y-x_1'},$$

for any $x'_2$, where $$C_f(x_2') = \frac{1}{\pi}\int_{-1}^{1}f(x_1'\theta_1+x_2'\theta_2)\,dx_1'. \qquad (5.\text{IV-7})$$

If we assume that the support of $f(x'_1\theta_1+x'_2\theta_2)$ as a functions of $x'_1$ is contained in $[-1,1]$ for any $x'_2$ then (IV-7) can be measured (FIG. 9a). Recall that $g_{\theta_1\theta_2}(x'_1, x'_2)$ is known for $x'_1 \leq x_0$. Then we can rewrite (IV-6) as $$\sqrt{1-x_1'^2}\,f(x_1'\theta_1+x_2'\theta_2) = C_f(x_2') + h_1(x_1', x_2') + h_2(x_1', x_2'), \qquad (5.\text{IV-8})$$

where $$h_1(x_1', x_2') = \frac{1}{\pi}PV\int_{-1}^{x_0}g_{\theta_1\theta_2}(y, x_2')\sqrt{1-y^2}\,\frac{dy}{y-x_1'}, \qquad (5.\text{IV-9})$$

$$h_2(x_1', x_2') = \frac{1}{\pi}PV\int_{x_0}^{1}g_{\theta_1\theta_2}(y, x_2')\sqrt{1-y^2}\,\frac{dy}{y-x_1'}. \qquad (5.\text{IV-10})$$

Here $h_1(x'_1,x'_2)$ is known for any $x'_1,x'_2 \in C$, because $g_{\theta_1\theta_2}(y, x'_2)$ is known for any $y \leq x_0$. Since it is given by a Cauchy type integral, $h_1(x'_1,x'_2)$ is an analytic function of $x'_1$ on C with a cut along $[-1, x_0]$. On the other hand, $h_2(x'_1,x'_2)$ is unknown because $g_{\theta_1\theta_2}(y,x'_2)$ is unknown for $y > x_0$. $h_2(x'_1,x'_2)$, however, is an analytic function of $x'_1$ on C with a cut along $[x_{0,1}]$. By (IV-8), $$h_2(x_1',x_2') = \sqrt{1-x_1'^2}f(x_1'\theta_1+x_2'\theta_2) - C_f(x_2') - h_1(x_1',x_2') \qquad (5.\text{IV-11})$$

is known on $[-1,x_0]$, because $f(x'_1\theta_1+x'_2\theta_2)$ vanishes on $[-1, x_0]$. The known values of $h_2(x'_1,x'_2)$ on $[-1,x_0]$ uniquely determine the analytic function $h_2(x'_1,x'_2)$ of $x'_1 \in C$ with a cut along $[x_{0,1}]$. What we need are values of $h_2(x'_1,x'_2)$ on the cut $[x_{0,1}]$, which are given by Theorem III-2:

$$h_2(x_1', x_2') = \frac{1}{2}\lim_{\substack{z \to x_1' \\ Im\,z>0}}h_2(z, x_2') + \frac{1}{2}\lim_{\substack{z \to x_1' \\ Im\,z<0}}h_2(z, x_2'). \qquad (5.\text{IV-12})$$

Substituting known values of $h_2(x'_1,x'_2)$ in (IV-12) into (IV-8), we can finally reconstruct $f(x'_1\theta_1+x'_2\theta_2)$ for $x'_1 \in [x_{0,1}]$ and any $x'_2$.

Figure 10:
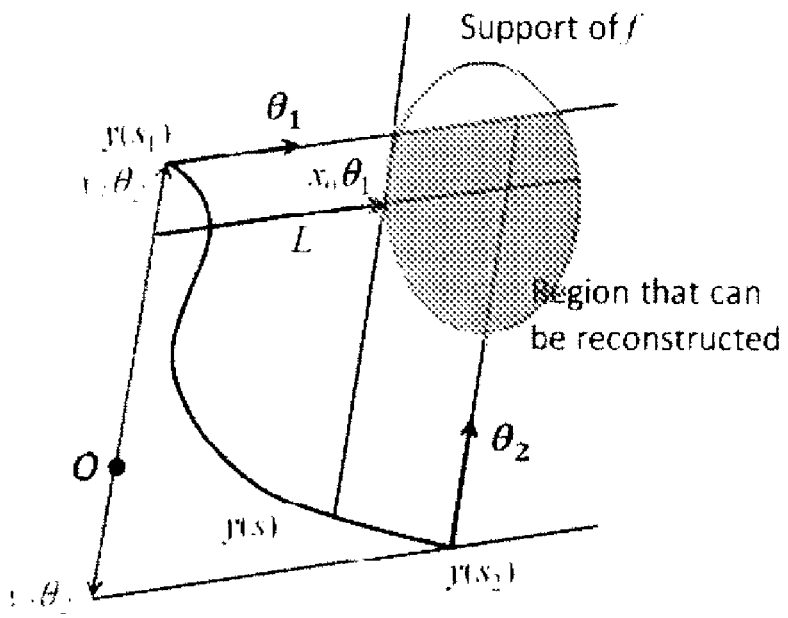
FIGS. 10A and 10B show regions in which (10A) the support of $f$ cannot be fully reconstructed by the limited-angle tomography and (10B) the support of $f$ may be fully reconstructed using different vectors $\theta_1$ and $\theta_2$.
Figure 10:
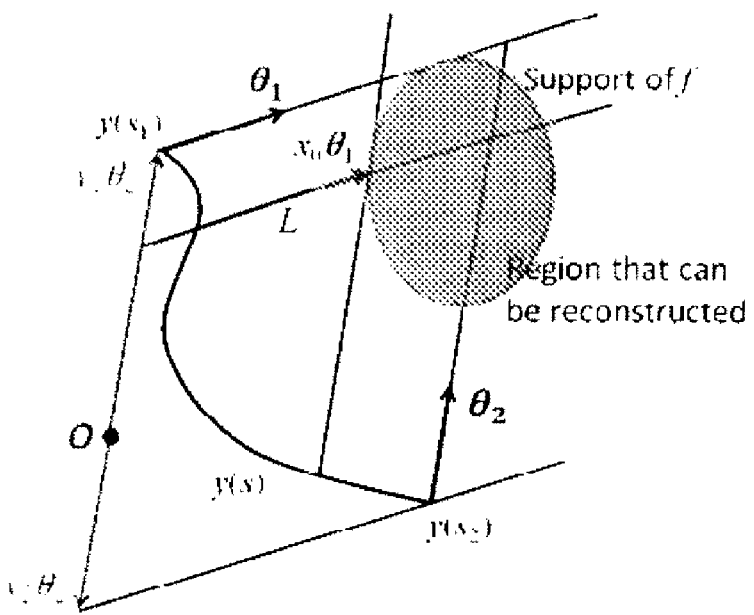

The reconstruction formula (IV-7-IV-12) needs a suitable scaling in the $\theta_1$ direction (FIG. 9). Since we need to know $C_f(x'_2)$ as in (IV-7), we have to rescale $\theta_1$ so that the support of $f(x'_1\theta_1+x'_2\theta_2)$ contained in $[-\theta_1,1, \theta_1 1]$. It is also possible to rescale the reconstruction formulas (IV-6) (FIG. 9b). The results are similar to those from rescaling $\theta_1$. If the support of $f$ is large, we may be able to reconstruct $f$ on its whole support or a portion of it by changing vectors $\theta_1$ and $\theta_2$ (FIG. 10).

Theorem IV-2. Let y(s), $s_1 \leq s \leq s_2$, be a smooth planar scanning curve, and let $\theta_1$ and $\theta_2$ be two non-parallel unit vectors as in FIGS. 9 and 10. Fix an origin O of the plane and write the end points of y(s) as linear combinations of $\theta_1$ and $\theta_2$: $y(s_j) = x_j\theta_1+y_j\theta_2$. Assume the support of the object function $f$ does not touch the scanning curve. Then $f(x'_1\theta_1+x'_2\theta_2)$ can be uniquely reconstructed for any $x'_1$, $x'_2$, with $x'_2$ lying between $y_1$ and $y_2$ by (IV-7)-(IV-12) after suitable rescaling.

This is a new proof of Hamaker's classical result (see Hamaker, C, et al., *The Divergent beam X-ray transform*. Rocky Mountain Journal of Mathematics, 1980. 10(1): p. 253-283).

To verify the theoretical results of limited-angle tomography, we developed a numerical interior tomography algorithm in an iterative framework. The algorithm consists of two major steps. In the first step, the ordered-subset simultaneous algebraic reconstruction technique (OS-SART) (see Wang, G. and M. Jiang, *Ordered-Subset Simultaneous Algebraic Reconstruction Techniques (OS-SART)*. Journal of X-ray Science and Technology, 2004. 12(3): p. 169-177) was used to reconstruct a digital image based on all the truncated local limited-angle projections. In the second step, compressive sensing techniques (see Donoho, D. L., *Compressed sensing*. Ieee Transactions on Information Theory, 2006. 52(4): p. 1289-1306, and Candes, E. J., J. Romberg, and T. Tao, *Robust uncertainty principles: Exact signal reconstruction from highly incomplete frequency information*. Ieee Transactions on Information Theory, 2006. 52(2): p. 489-509) were used to minimize the total variation to improve the reconstructed image quality based on the Hilbert transform constraints. These two steps were iteratively performed in an alternating manner. Our algorithm was numerically implemented in MatLab on a PC (1.0 Gigabyte memory, 2.8 G Hz CPU). While the basic structure was constructed in MatLab, all the computationally intensive parts were coded in C, which was linked via a MEX interface. A maximal iteration time was set to stop the main loop.

Figure 11:
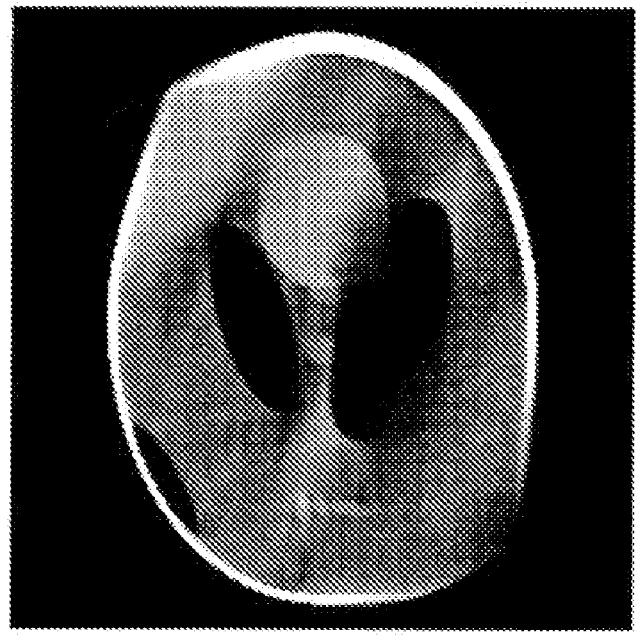
FIG. 11 show reconstructed head phantom images from limited-angle projections. 11A is a reconstruction by the classic SART method; and 11B was reconstructed by our limited-angle reconstruction technique utilizing compressed sensing theory as well as prior knowledge.
Figure 11:
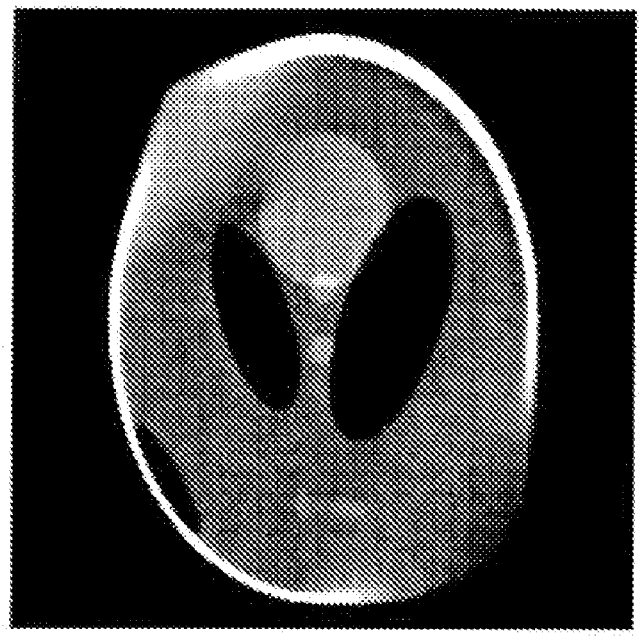

In our numerical simulation, we assumed a circular scanning locus of radius 57.0 cm and a fan-beam imaging geometry. We also assumed an equi-spatial virtual detector array of length 20.0 cm. The detector was centered at the system origin and made always perpendicular to the direction from the system origin to the x-ray source. The detector array included 600 elements, each of which is of aperture 0.033 cm. This scanning configuration covered a circular FOV of radius 10.0 cm. For a quarter scanning turn (90 degree), we equi-angularly collected 400 projections. The reconstructed object was a 2D modified Shepp-logan phantom (see Shepp, L. A. and B. F. Logan, *The Fourier Reconstruction of a Head Section*. IEEE Transactions on Nuclear Science, 1974. NS21(3): p. 21-34) whose radius was also 10.0 cm. This phantom is piecewise constant and includes a set of smooth ellipses. To verify the proposed algorithm, we initially only performed the OS-SART reconstruction, then introduced the regularization of the total variation and Hilbert transform. Both of the reconstructed images are in a 256×256 matrix covering a FOV of radius 10 cm (see FIG. 11). As seen in FIG. 11, the proposed algorithm has a better performance than OS-SART technique.

Section V

Instant/Ultrafast Tomography

Another improvement to our interior tomographic techniques is an instant tomography technique which relies on the interior tomography approach described above. This instant/ultrafast tomography methodology is described in greater detail below.

With interior tomography a small ROI can now be irradiated with much narrower beams, meaning that smaller detectors can be employed, and many x-ray source-detector pairs can be assembled into a single system. Parallel data acquisition can be implemented using many compact x-ray sources such as Carbon nano-tube-based x-ray sources (see Chang, S., et al, *Development of a carbon nanotube based low-LET multi-pixel microbeam array*. Rad. Res., 2006. 166(12): p. 658-659; also, private communications with Dr. Otto Zhou, University of North Carolina), and corresponding small detectors delimited by the x-ray shadow of the ROI.

Figure 12:
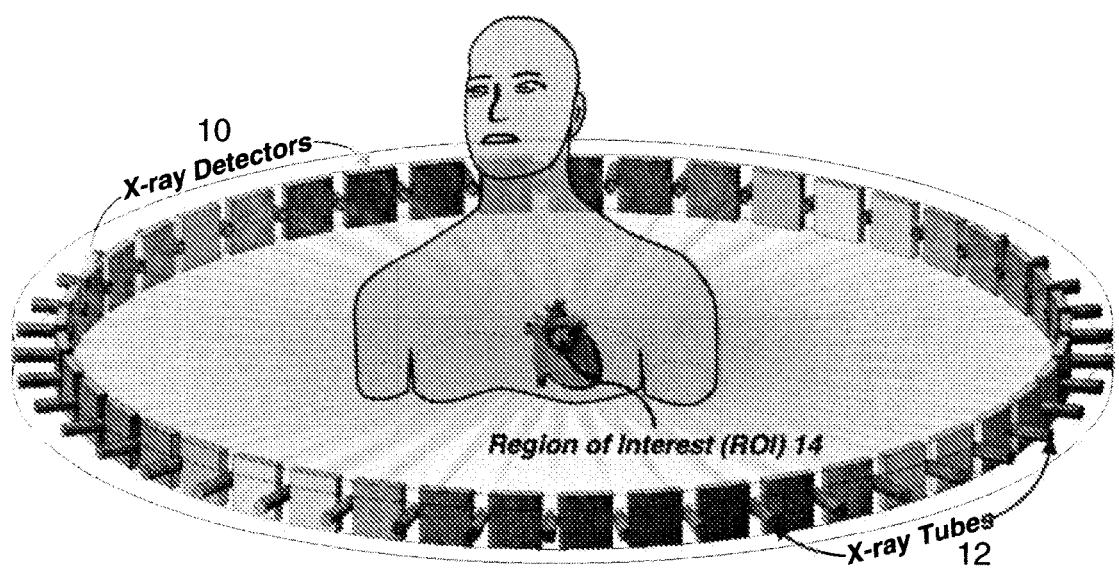
FIG. 12 is a diagrammatic illustration of instant tomography for cardiac imaging using the interior tomography approach, wherein the detector size can be greatly reduced so that many source-detector pairs can be fit together to focus on a ROI for simultaneous collection of enough local projections without any source scanning.

This concept is illustrated by an example in FIG. 12, which shows a concept of instant tomography for cardiac imaging. With the interior tomography approach, the detector size can be greatly reduced so that many source-detector pairs can be fitted together to focus on an ROI for simultaneous collection of enough local projections without any source scanning. Hence, sufficient data can be acquired with a much shorter source scan or even without any scanning for unprecedented "instant tomography" of such the small ROI, which can be then roamed to visualize physiologic/pathological features inside a large space. Therefore, the resultant reconstruction of the ROI will have a temporal resolution of nearly zero. Note that gaps between detector elements 10 due to the x-ray sources 12 would not cause additional data truncation, since each source and detector pair (a pair being a source and detector along a line passing through the body) is fixed. Further, the X-ray beam or other radiant energy beam can be well collimated and focused on an ROI inside the object such as a patient so that the ROI will be projected into the interior of the mini-detectors as is shown in FIG. 12.

If conventional sources are used in FIG. 12, they would subtend a significant solid angle, leading to a reduction in angular sampling, but emerging nano-tube or other innovative sources may not yet immediately have a sufficient flux required for demanding clinical applications. Potentially, our scheme can be modified in a number of ways, such as distributing sources on a cylindrical surface around an ROI or VOI in the patient, using source segments on which focal spots can be sequentially fired (brighter than current nano-tubes), improving nano-tubes' brightness or even inventing sources and detectors that allow new imaging possibilities.

For purposes of this application, performing interior tomography in a parallel fashion will include both simultaneous and sequential firing of sources through the ROI.

To demonstrate the feasibility of our instant interior tomography, we performed a CT experiment with a living sheep, which was approved by Virginia Tech IACUC committee (exempt review). The chest of a sheep was scanned in fan-beam geometry on a SIEMENS 64-Slice CT scanner (100 kVp, 150 mAs). The radius of the x-ray source trajectory was 570 mm. There were 1160 projections uniformly collected over a 360° range, and 672 detectors were equi-angularly distributed per projection. The radius of the field of view (FOV) was 250.5 mm. First, an entire 290.56 mm by 290.56 mm cross-section was reconstructed into 1024×1024 pixels using the popular FBP method from complete projections. Second, a trachea in which we already knew the CT number of the internal air was selected in reference to the reconstructed image. Around the trachea, we specified a circular ROI of radius 120 pixels and kept only the projection data through the ROI. Third, interior tomography of the ROI was performed with the same pixel size as for the global reconstruction on 580 groups of parallel lines through the known trachea region, and these groups are uniformly distributed along the full scan range. Each group included 16 uniformly distributed parallel lines. On each line, we converted the reconstruction problem into a regularization problem in the framework of a truncated Hilbert transform and determined the solution by the singular value decomposition (SVD) (see Hengyong Yu, Yangbo Ye and Ge Wang; Interior reconstruction using truncated Hilbert transform via singular value decomposition; Journal of X-ray Science and Technology, 16(4):243-251, 2008). Finally, the redundant reconstruction results were averaged to optimize the image quality. Note that each of the parallel lines in the 580 groups serves as the chord under reconstruction, on which a full-resolution backprojection and filtration (or full-resolution backprojection of differential data) were performed and averaged at each point in the ROI.

Figure 13:
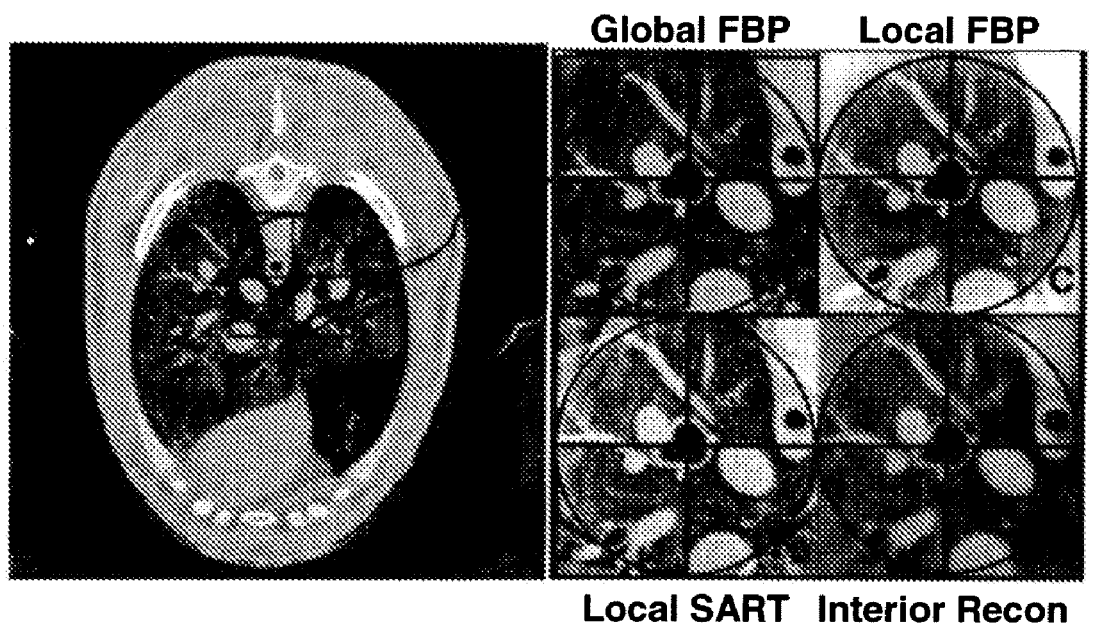
FIGS. 13A to 13G are a feasibility demonstration of interior reconstruction with a lung CT scan.
Figure 13:
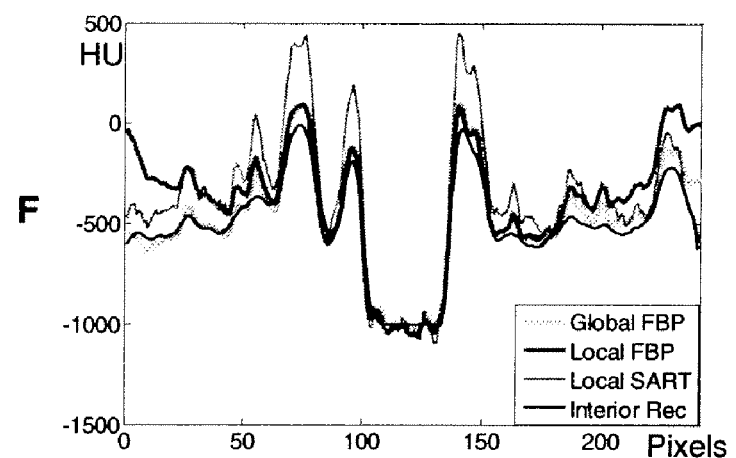
Figure 13:
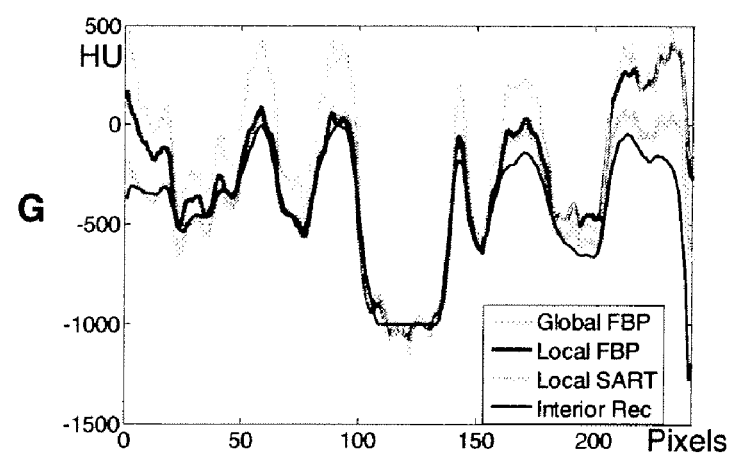

Our method produced an excellent ROI reconstruction that was previously impossible and yet ran two orders of magnitude faster than the iterative approaches. For comparison between our approach and existing approximate local reconstruction algorithms, we adapted the popular filtered backprojection (FBP) algorithm and simultaneous algebraic reconstructive technique (SART) (see G. Wang and M. Jiang, *Ordered-Subset Simultaneous Algebraic Reconstruction Techniques (OS-SART)*. Journal of X-ray Science and Technology, 2004. 12(3): p. 169-177). The FBP was applied after the truncated data were sinusoidally extrapolated to zero. The SART was accelerated using the ordered-subset technique (10 subsets and 60 iterations). The representative images and profiles are shown in FIG. 13. Also, we examined key image quality indexes of each reconstruction in FIG. 13, using the global FBP reconstruction as the baseline. The results are summarized in Table 1. The resolution was statistically estimated orthogonally across the internal borders of the trachea and its nearest disconnected major blood vessel as the full-width-of-half-maximum (FWHM) of the line response function fitted into the Gaussian function (see F. J. Schlueter, et al., *Longitudinal Image Deblurring In Spiral Ct*. Radiology, 1994. 193(2): p. 413-418). The noise was computed as the standard deviation σ in a flat blood region. Clearly, interior tomography performed much better than either of the competing brute-force algorithms. Surprisingly, it performed even better than the global FBP reconstruction in terms of resolution and noise, most likely because the exact knowledge of the trachea helped regularize interior tomography to yield more favorable resolution and noise in the ROI around the trachea.

TABLE 1

Algorithm comparison for interior reconstruction in terms of the mean error $\bar{\epsilon}$, maximum error $\epsilon_{max}$, image resolution, and noise..

|  | $\bar{\epsilon}$ (HU) | $\epsilon_{max}$ (HU) | Resolution (mm) | Noise σ (HU) |
| --- | --- | --- | --- | --- |
| Global FBP Recon | 0.0 | 0.0 | 1.540 | 34.1 |
| Local FBP Recon | 161.9 | 439.9 | 1.566 | 49.1 |
| Local SART Recon | 198.5 | 583.6 | 1.538 | 56.7 |
| Interior Recon | 84.6 | 434.8 | 1.487 | 21.0 |

Figure 14:
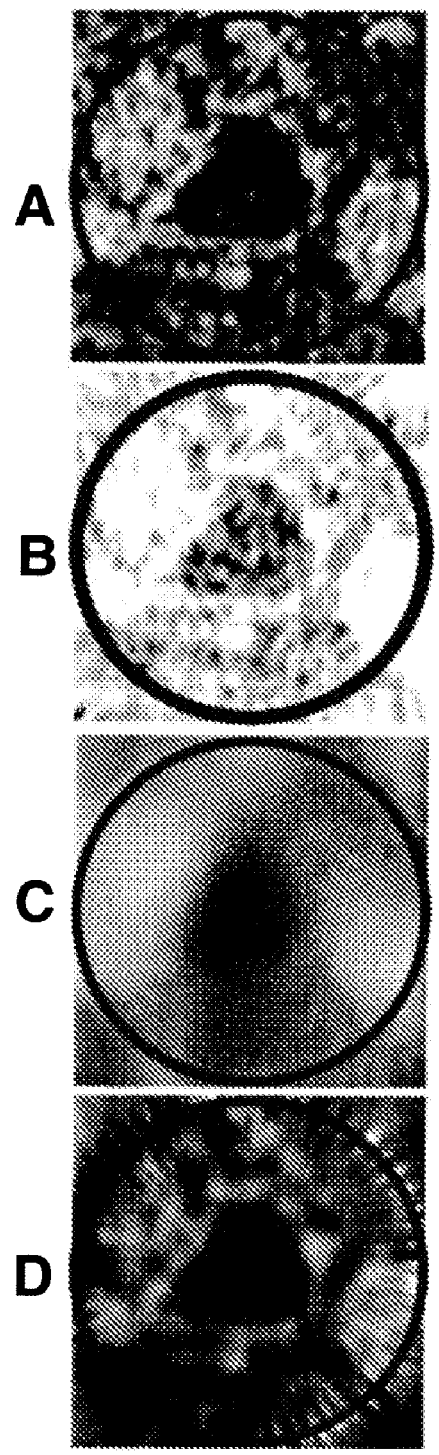
FIGS. 14A to 14D are a series of images demonstrating instant interior reconstruction of an ROI with a realistic data acquisition setup, sampled from a sheep lung scan using only 1 in every 20 projections in the full scan range. (14A) Global FBP reconstruction from the complete data set is used as a gold standard for the local reconstructions using (14B) FBP, (14C) SART, and (14D) interior tomography techniques.

Next, let us examine a data acquisition issue further for instant tomography illustrated in FIG. 12. Using the same sheep lung CT scan, the above simulation was repeated in a realistic parallel fashion. The raw data was sampled from the sheep lung scan using only 1 in every 20 projections in the regular full scan. Assuming each projection corresponded to an appropriate detector array segment, and the x-ray tubes took up no room on the gantry, a centralized ROI of radius 15.4 mm (the gantry is assumed to be of radius 570 mm) would be well illuminated. Then, 58 projections were uniformly selected from the 1160 views by discarding 19 projections in every 20 projections. With the same pixel size as in the previous reconstruction, the ROI was of radius 54 pixels. Then, interior tomography of the ROI was performed on 58 groups of parallel lines and each group included 22 uniformly distributed parallel lines. The final results are shown in FIG. 14, where the SART result was produced after 200 iterations. The global FBP reconstruction from the complete data set as a gold standard, shown in FIG. 14A. The remaining 3 images show 3 techniques for local/interior reconstruction: FIG. 14B is the local reconstructions using the FBP (after smooth data extrapolation), FIG. 14C is SART (with ordered subsets) and FIG. 14D is interior tomography. The display window remains [−800HU, 700HU] for each. Although the image artifacts in FIG. 14 are more evident than that in FIG. 13, these results support this prototypical instant tomography— the perfect temporal resolution is indeed achieved. Unlike popular tomosynthesis techniques, instant tomography allows symmetric data acquisition, avoiding major biases from primary viewing directions associated with a tomosynthetic scan. More importantly, it is very hopeful that next generation reconstruction algorithms may produce much better image quality from a limited number of projections than it is possible now. For example, compressive sensing/sampling theory suggests that reconstruction quality may be maintained after a dramatic reduction in the number of projections (G. H. Chen, J. Tang, and S. H. Leng, *Prior image constrained compressed sensing (PICCS): A method to accurately reconstruct dynamic CT images from highly undersampled projection data sets*. Medical Physics, 2008. 35(2): p. 660-663; M. Lustig, D. Donoho, and J. M. Pauly, *Sparse MRI: The application of compressed sensing for rapid MR imaging*. Magnetic Resonance in Medicine, 2007. 58(6): p. 1182-1195; H. Jung, et al., *k-t FOCUSS: A general compressed sensing framework for high resolution dynamic MRI*. Magnetic Resonance in Medicine, 2008, to appear).

Figure 15:
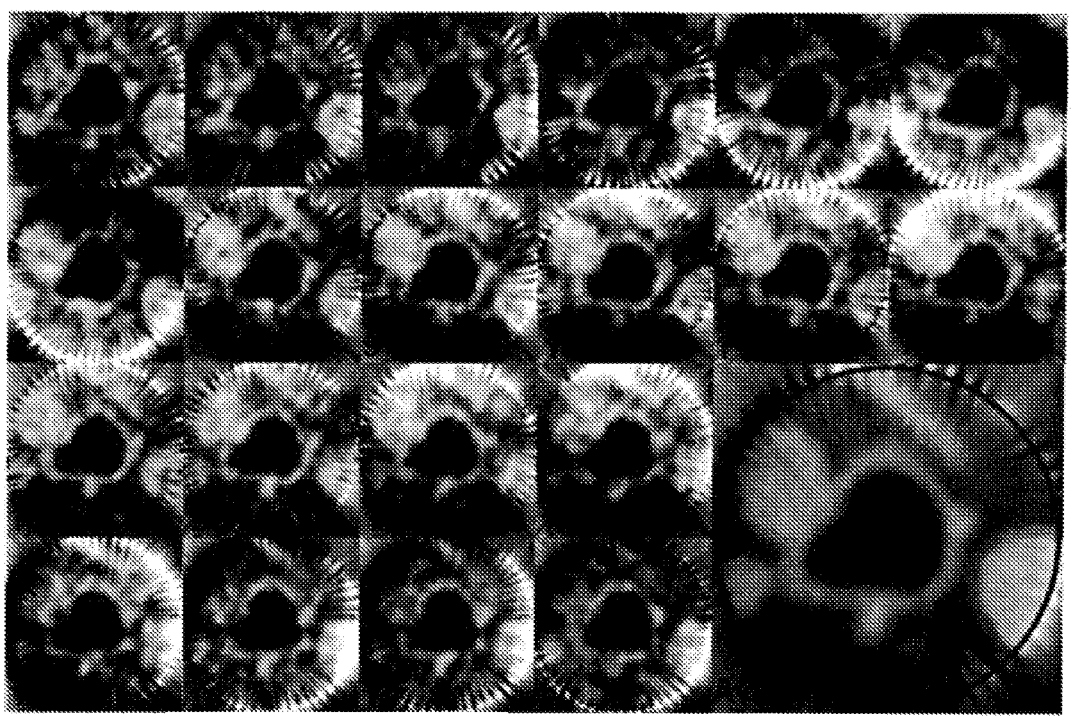
FIG. 15 is a series of images further demonstrating instant interior reconstruction with a realistic data acquisition setup, in which raw data was repeatedly sampled from a sheep lung scan using only 1 in every 20 projections in the full scan range, generating 20 reconstructions to synthesize a higher quality snapshot.

An effective way to improve the image quality of instant tomography such as that shown in FIG. 14D is to average multiple instant snapshots of the same ROI. This idea is demonstrated in FIG. 15, which also illustrates instant interior reconstruction with a realistic data acquisition setup. The raw data was repeatedly sampled from the sheep lung scan using only 1 in every 20 projections in the regular full scan. The images in FIG. 15 show 20 reconstructions and their average image. All display windows are [−800HU, 700HU]. The key is to acquire instant datasets independently and align these datasets in a common coordinate system. In this context, image registration techniques will play a critical role. Furthermore, next generation reconstruction algorithms can produce much better image quality from a limited number of projections than it is possible now, and it should be understood that the invention would include variations in the use of such algorithms to improve image quality.

Another effective way to suppress image artifacts and/or increase the FOV is to use detectors in a time-sharing fashion which can also be referred to as a source-multiplexing scheme. Similar to the Hadamard multiplexing method developed by Dr. Otto Zhou's group (Zhang, J., et al. Hadamard multiplexing radiography based on carbon nanotube field emission multi-pixel x-ray technology. Proceedings of SPIE, Vol. 6913, Article ID: 69131T, 2008), we can arrange p×q x-ray focal spots around a subject, along with the corresponding detectors. Under the computer control, we can electronically trigger p x-ray sources simultaneously for q times to produce projection data continuously on its associated detectors. In this way, each detector will be used by q x-ray focal spots in q consecutive time slots. Note that this method can not only improve image quality but also avoid the conflict between the ROI size and number of focal spots that are on at the same time.

Figure 16:
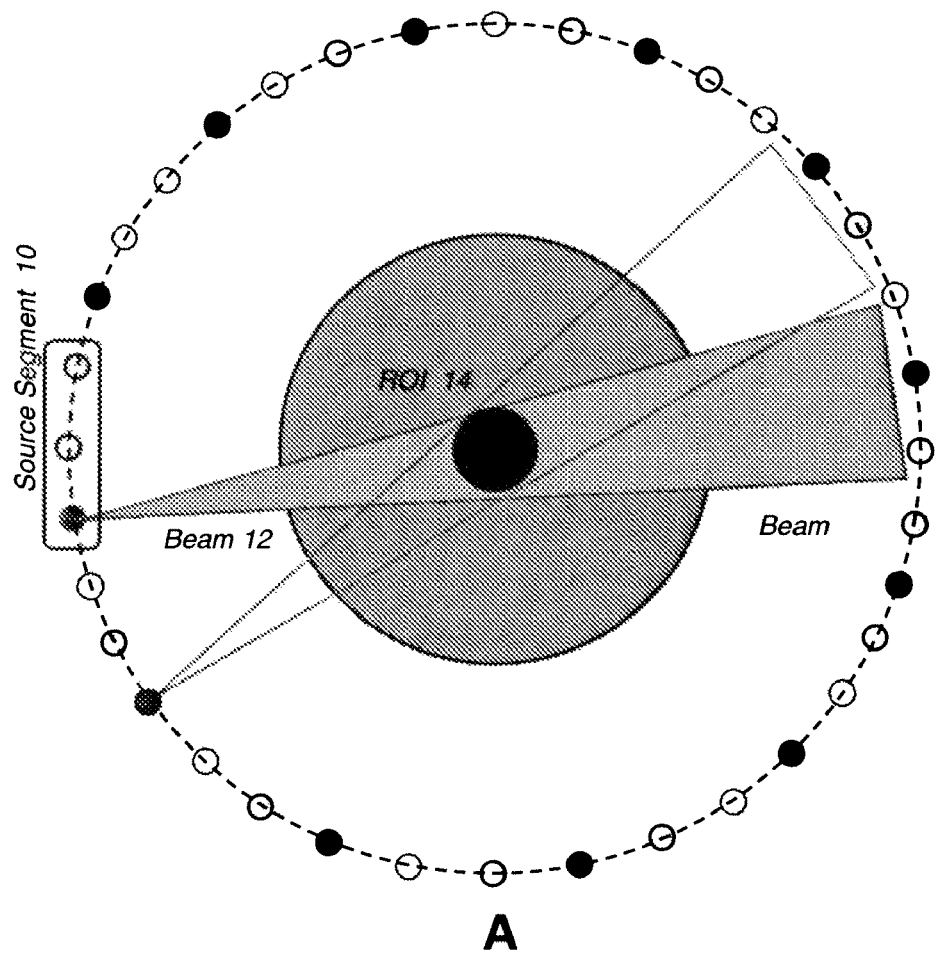
FIG. 16 is demonstration for field of view (FOV) increment using a parallel source-multiplexing scheme. (16A) A simple example of source multiplexing where 36 x-ray focal spots are distributed around a subject targeting a central ROI from 12 source segments of 3 focal spots per segment. In this scheme, only one focal spot in each of the source segments is turned on in one time slot, and the scan is finished in 3 consecutive time slots which can be done ultrafast such as with the nano-tube based source array technology (REF); in a more realistic 1 in every 4 projections was selected from the sheep lung scan to simulate 290 x-ray sources around the subject from 29 source segments of 10 focal spots per segment with (16B) the global FBP reconstruction from the complete dataset as the gold standard; 16C-16E the local reconstructions using FBP (after smooth data extrapolation), SART (with ordered subsets) and interior tomography techniques, respectively. The display window is [−800HU, 700HU].
Figure 16:
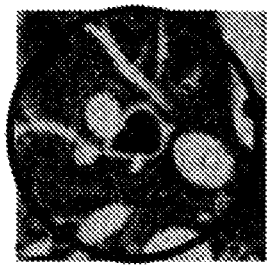
Figure 16:
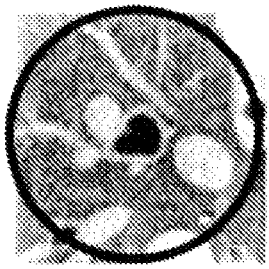
Figure 16:
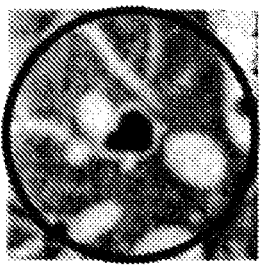
Figure 16:
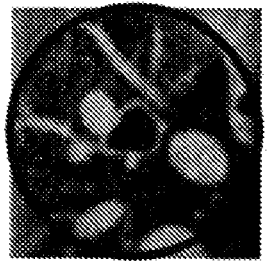

This source-multiplexing idea is illustrated in FIG. 16a, along with a realistic simulation (FIGS. 16b-e) where 290 x-ray sources were assumed to illustrate an ROI of radius 30.9 mm by setting q=10 for the gantry of radius 570 mm. While this multiplexing scheme is not instant, it can acquire a complete dataset at speed 1-2 orders of magnitude faster than that of the state-of-the-art CT scanner.

Figure 17:
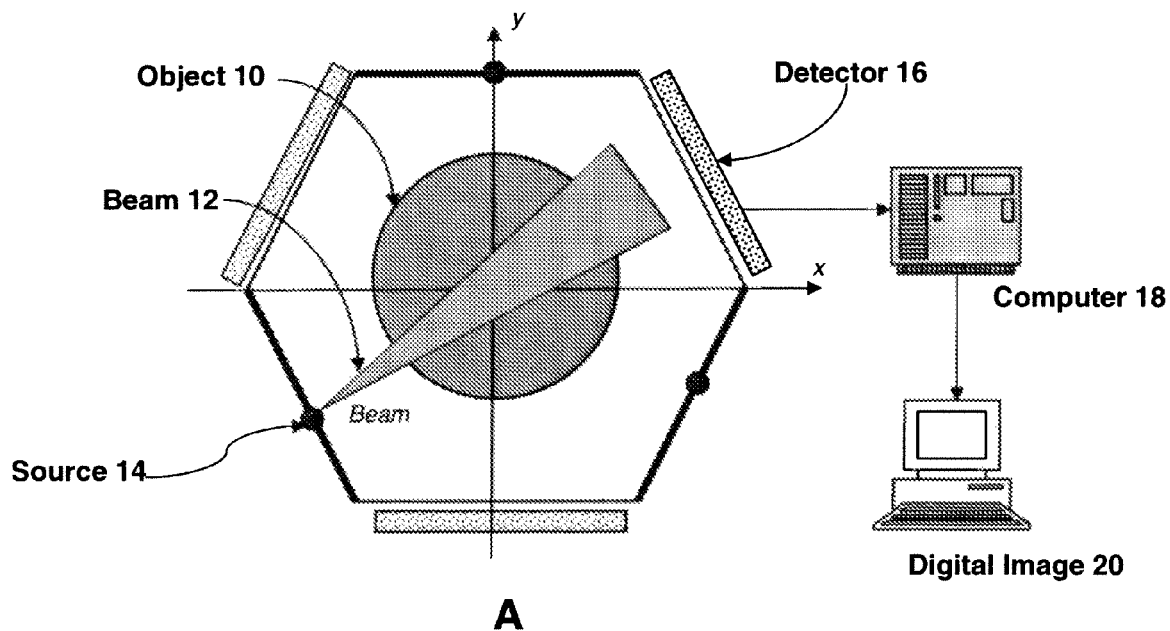
FIG. 17 are practical system configurations. (17A) Triple line/arc-sources are symmetrically arranged, along with the corresponding detector arrays around an object to be reconstructed, and (17B) all the sources are grouped on one side while the detectors on the other. On the source segment, multiple focal spots can be turned on simultaneously to utilize the detectors effectively. Multiplexing of the available focal spots will collect adequate fan-beam or cone-beam projection data for limited angle interior tomography. Note that the Tuy condition is satisfied in a centralized ROI if its size is sufficiently small. Practically, an excellent image quality can be achieved in a relatively small central ROI. Other polynomial or curved arrangements of sources and detectors can be made in the same spirit of this invention.
Figure 17:
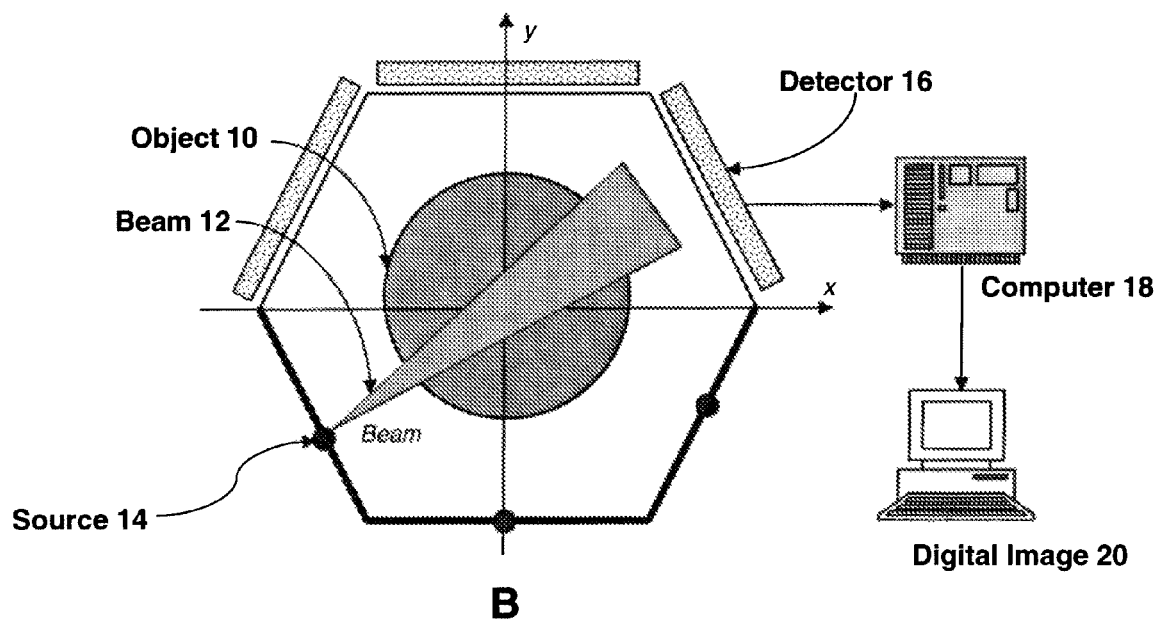

Two attractive time-sharing/multiplexing designs are shown in FIG. 17, where we use three line-source segments coupled by three detectors. The source-detector pairs are shown in arrays surrounding an Object 10 to be scanned, with a smaller ROI within Object 10. When the ROI is smaller and closer to the iso-center of Object 10, the reconstruction quality is improved, since the stability of the solution to the limited data problem would be higher in general. A known subregion within the ROI can be used as a landmark for image reconstruction. X-ray sources are arrayed singly or in groups, as represented by Source 12, which may be one or a plurality of sources. Beam 14 is emitted from Source 12, and can be emitted simultaneously or sequentially with other sources in the the arrays surrounding Object 10. Beams can be truncated limited-angle beams. Beam 14 is detected by Detector 16, and other beams can be detected simultaneously or sequentially by detectors that are placed in opposing positions to other beams emitted by the array of sources. The data acquired by Detector 16 from the projection of Beam 14 is transmitted to Computer 18 for computational analysis and integration. The integrated data is used to reconstruct Digital Image 20, which can be visualized on a computer screen or other electronic device. An alternative configuration source-detector pairs is shown in FIG. 17B. These designs can be easily implemented using off the shelf components. Then, ultrafast tomography can be achieved within an ROI using our disclosed limited-angle interior reconstruction approach.

While the presented results showing the feasibility of interior/instant tomography are encouraging, a critical examination indicates that the current interior tomography technology is not perfect, as evidenced by the lack of details and residual artifacts in the peripheral region in the interior reconstruction. This sub-optimal performance is due to the fact that the stability analysis of the current interior tomography technique reveals that the reconstruction error would increase further away from the sub-region on which we have exact knowledge. Certainly, there are opportunities to improve the image quality using more advanced algorithms and it should be understood that the invention would include variations in the use of such algorithms to improve image quality. A more detailed analysis of the x-ray dose associated with instant tomography is also needed. For example, one needs to position the "imaging window" of instant tomography inside the organ of interest. If this organ is moving (e.g., in cardiac applications) and the window is sufficiently small, significant dose could be wasted on accidental imaging outside of the target area. However, if we are roaming the ROI around in the patient, much of these "wasted margins" for one ROI can be effectively utilized for other ROIs. For that purpose, we can develop a deformable model and registration approach. Actually, both tremendous biomedical imaging needs for interior tomography and this type of flaws in image quality and dose utilization with interior tomography indicate potentials to advance this new area and capitalize its major benefits in clinical/preclinical and other applications.

One may worry that the scatter with the multi-source interior tomography system would be extremely high. Actually, this is not the case. Briefly speaking, the larger the number of sources is (which is typically odd), the narrower each x-ray beam ($\pi/N$), and the smaller the FOV. Clearly, the scatter in the data is roughly proportional to the product of the number of sources and the beam width (which is proportional to the size of the FOV). Thus, the scatter to primary ratio cannot go infinite as the number of sources is increased, since basically the beam width is inversely proportional to the number of sources. Also, detector collimation can be used to reject scattered photons, and electronic multiplexing can be added to turn these x-ray sources on and off selectively and rapidly, if scattering needs to be minimized. Furthermore, the dose to the patient (inside and outside the ROI) from N truncated projections is smaller (in the ROI) or much smaller (outside the ROI) than that from N non-truncated projections.

Interior/instant tomography is highly desirable in a number of disciplines. Let us comment on a few of such examples. First, instant tomography may revolutionize cardiac CT. Cardiovascular diseases are pervasive, producing high mortality and morbidity at tremendous social and healthcare costs (www.americanheart.org). Current cardiovascular research aims to improve our understanding of the pathobiology and genetics of coronary artery diseases. Cardiac CT has emerged as a promising tool for noninvasive coronary angiography (see Naghavi, M., et al, *From vulnerable plaque to vulnerable patient—A call for new definitions and risk assessment strategies: Part I. Circulation,* 2003. 108(14): p. 1664-1672). Electron-beam CT was the first dedicated cardiac CT modality with temporal resolution as low as 50 ms, but it has essentially become obsolete largely because of major limitations in spatial and contrast resolution. State-of-the-art medical CT scanners can achieve temporal resolution of 100 ms. However, given the rate and magnitude of the cardiac motion, temporal resolution should ideally be <10 ms for humans and <2 ms for small animals such as rats and mice. Achieving these resolutions have been extremely challenging. Our interior tomography approach makes an instantaneous snapshot of an ROI to assess the calcium burden and vascular stenoses, to identify positive remodeling and plaque consistency, etc., especially in cases of high/irregular heart rates, contrast-enhanced CT scans and small animal studies.

Second, instant tomography may enable clinical and pre-clinical micro-CT such as for inner ear imaging (see Wang, G, et al, *Design, analysis and simulation for development of the first clinical micro-CT scanner. Academic Radiology,* 2005. 12(4): p. 511-525). Two major obstacles in achieving such fine spatial resolution in vivo are physiological motion blurring (the smaller the imaging scale, the more significant the physiological motion in an order of millimeter) and radiation dose limitation (the finer the resolution, the greater the radiation dose). When an x-ray beam is defined by a small ROI and projections are acquired in parallel, both of the above two issues are effectively addressed at the same time, which may help derive image-based biomarkers for many applications in diagnosis and therapy. Similarly, the ability to reconstruct exactly a small ROI inside a larger object with a narrow x-ray beam is essential to advancing nano-medicine development. The state-of-the-art nano-CT scanners allow an FOV of ~20 $\mu m^3$. To image a nano-medicine specimen, the current technology requires sectioning it into a small segment down to the size of the FOV. Actually, at the 8 keV energy of nano-CT, organs/tissues of interest have over 1 mm attenuation length (see Wang, Y. X., W. B. Yun, and C. Jacobsen, *Achromatic Fresnel optics for wideband extreme-ultraviolet and X-ray imaging. Nature,* 2003. 424(6944): p. 50-53), suggesting that samples of several mm thickness can be examined without sectioning. Hence, interior tomography is capable of imaging deeply embedded nano-structures non-invasively to maintain specimen integrity and hydration, minimize radiation damage and image artifacts, as well as reduce operation time and system cost. That is, interior tomography will provide a freshly new way to study cellular and molecular features of nano-medicine specimens in their native states.

Third, biomedical interior tomography of the lung, heart, head, and neck can dramatically reduce CT radiation exposure to a patient. This is highly desirable, particularly in screening, perfusion and follow-up studies because of the heated public debate surrounding a recent high-profile article on the rapid growth of CT use and its associated radiation risks (see Brenner, D. J. and E. J. Hall, *Current concepts—Computed tomography—An increasing source of radiation exposure. New England Journal of Medicine,* 2007. 357(22): p. 2277-2284). Statistical methods for interior tomography can reduce the radiation dose further.

In the above and other scenarios, interior tomography is a powerful, even necessary, tool to reduce radiation dose (no x-rays go outside the ROI), suppress scattering artifacts (no interference or cross-talk from radiation outside the ROI), refine image quality (by the new reconstruction approach and exact prior knowledge), handle large objects (measurement can be localized in any direction), decrease engineering cost (with smaller detectors and more compact system design), increase system functionalities (with more flexible architectures), boost scanner throughput (due to minimized and accelerated data flows), and achieve ultrafast or instant tomography (using many source-detector pairs).

The invention claimed is:

1. The method for limited-angle interior tomography, comprising the steps of:
   a) identify a region of interest (ROI) in an object;
   b) measure truncated differences of Hilbert transform data through the ROI where the data are defined by the equation $$\int_{s_1}^{s_2} \frac{d}{dh} D_f(s, P - y(s) + hy'(s)) \bigg|_{h=0} ds + \qquad (5.1)$$
$$D_f(s_2, P - y(s_2)) - D_f(s_1, P - y(s_1)) =$$
$$z \frac{1}{\pi} PV \int_{\mathcal{A}} \frac{f(P - t\theta_2)}{t} dt - \frac{1}{\pi} PV \int_{\mathcal{A}} \frac{f(P - t\theta_1)}{t} dt.$$

where $f$ is the object function representing the linear attenuation coefficient, $D_f$ is the measured projection data, PV represents the principal value, $y(s)$, $s_1 \leq s \leq s_2$, is a scanning curve, P is a point in the ROI, and $\theta_j$ is a unit vector from $y(s_j)$ to P;
   c) determine or acquire a linear attenuation coefficient distribution of a subregion in the ROI;
   d) reconstruct the ROI according to measured truncated differences of Hilbert transform data and said linear attenuation coefficient property for said subregion.

2. The method of claim 1 wherein the said limited scanning angle is less than 180 degrees for some regions, and is 180 degrees for the other regions.

3. The method of claim 1 wherein said subregion is a single point.

4. The method of claim 1 wherein said subregion is a collection of sampling points.

5. The method of claim 1 wherein said subregion is less than 5% the size of said ROI.

6. A method of performing interior tomography of a region of interest (ROI) in a parallel-fashion using an interior tomography, comprising the steps of:
   a) simultaneously or sequentially probing an ROI with multiple x-ray or similar beams at multiple angles extending through a said ROI and collecting data from said multiple x-ray beams;
   b) identifying a linear attenuation coefficient distribution for at least one sub-region in said ROI; and
   c) using an interior tomography algorithm to reconstruct the ROI.

7. The method of claim 6 wherein said step of simultaneously or sequentially probing is performed using a series of sources and detectors which encircle a body in which the ROI is located.

8. The method of claim 6 wherein said step of identifying an ROI uses a scan of a body containing said ROI taken before said step of simultaneously probing, and includes the step of identifying one or more of air gaps or voids, water, blood or other liquid, or other calibrated structures including implants, or a known sub-region, or also including acquisition of other forms of knowledge such as low-resolution version of the ROI or a super set of the ROI.

9. The method of claim 6 wherein said ROI is a portion of a heart, an ear, or of bony structures in a patient.

10. The method of claim 6 further comprising the step of moving/roaming said ROI to a new location within a body by moving said body within a tomographic system or by moving said tomographic system relative to said body and repeating steps a-c.

11. The method of claim 6 wherein limited angle interior tomography is used, said limited angle interior tomography including the steps of:
   a) identify a region of interest (ROI) in an object;
   b) measure truncated differences of Hilbert transform data through the ROI where the data are defined by the equation $$\int_{s_1}^{s_2} \frac{d}{dh} D_f(s, P - y(s) + hy'(s)) \bigg|_{h=0} ds +$$
$$D_f(s_2, P - y(s_2)) - D_f(s_1, P - y(s_1)) =$$
$$z \frac{1}{\pi} PV \int_{\mathcal{A}} \frac{f(P - t\theta_2)}{t} dt - \frac{1}{\pi} PV \int_{\mathcal{A}} \frac{f(P - t\theta_1)}{t} dt$$

where $f$ is the object function representing the linear attenuation coefficient, $D_f$ is the measured projection data, PV represents the principal value, $y(s)$, $s_1 \leq s \leq s_2$, is a scanning curve, P is a point in the ROI, and $\theta_j$ is a unit vector from $y(s_j)$ to P:
   c) determine or acquire a linear attenuation coefficient distribution of a subregion in the ROI;
   d) reconstruct the ROI according to measured truncated differences of Hilbert transform data and said linear attenuation coefficient for said subregion.

12. The method of claim 6 wherein limited angle interior tomography is used, said limited angle interior tomography including the steps of:
   a) identify a region of interest (ROI) in an object;
   b) measure truncated Hilbert transform data defined by $$g(y) = \frac{1}{\pi} PV \int_{c_1}^{c_2} f(x) \frac{dx}{y - x} (H_L f)(y),$$
$$y \in (c_3, c_4), c_1 < c_3 < c_5 < c_4 < c_2$$

where $f$ is the object function representing the linear attenuation coefficient, $H_L$ represent Hilbert transform, PV represents the principal value, $(c_1, c_2)$ is an object support, $(c_3, c_4)$ is a segment in said ROI, $(c_3, c_5)$ is a known portion in the segment, and the interior reconstruction is performed using SVD or similar techniques.
   c) determine or acquire a linear attenuation coefficient for a subregion of the ROI;
   d) reconstruct the ROI according to singular value decomposition using said linear attenuation coefficient for said subregion.

13. A system for performing interior tomography of a region of interest (ROI), comprising:

a) a plurality of x-ray source and detector pairs for simultaneously or sequentially probing an ROI with multiple x-ray beams at multiple angles extending through said ROI;

b) a computer for collecting data from said multiple x-ray beams obtained from said detectors which uses an interior tomography algorithm to reconstruct the ROI using a linear attenuation coefficient that is known for at least one sub-region in said ROI that is of a non-zero measure.

14. The method for limited angle interior tomography, comprising the steps of:

b) identify a region of interest (ROI) in an object;

b) measure truncated Hilbert transform data defined by $$g(y) = \frac{1}{\pi} PV \int_{c_1}^{c_2} f(x) \frac{dx}{y-x} = (H_L f)(y),$$

$$y \in (c_3, c_4), c_1 < c_3 < c_5 < c_4 < c_2$$

where $f$ is the object function representing the linear attenuation coefficient, $H_L$ represent Hilbert transform, PV represents the principal value, $(c_1, c_2)$ is an object support, $(c_3, c_4)$ a segment in said ROI, $(c_3, c_5)$ is a known portion in the segment, and the interior reconstruction is performed using SVD or similar techniques.

c) determine or acquire a linear attenuation coefficient for a subregion of the ROI;

d) reconstruct the ROI according to singular value decomposition using said linear attenuation coefficient for said subregion.

15. The method of claim 14 wherein the objective function is a regularization scheme defined by $$\hat{A}_u = \underset{A_u}{\operatorname{argmin}}(\|\bar{B} - H_u A_u\|^2 + \xi^2 \|LA_u\|^2)$$

where L and $\xi$ are a regularization constraint and a relaxation coefficient respectively, and the remaining constituents are derived from a Hilbert transform, which can be augmented by projection transform data, represented as B=HA, where H is a coefficient matrix corresponding to the Hilbert transform kernel, and A is divided into the known and unknown parts $A_k$ and $A_u$, and H is divided into $H_k$ and $H_u$ such that $\bar{B}=B-H_k A_k=H_u A_u$ a linear inversion problem, and because all the rows of $H_u$ are formed by the truncated discrete Hilbert transform kernel (if it is augmented by the projection data, the projection transform coefficients are also assumed known), one can utilize the properties of $H_u$ to solve the unknown $A_u$ from the known $\bar{B}$.

* * * * *

UNITED STATES PATENT AND TRADEMARK OFFICE
CERTIFICATE OF CORRECTION

PATENT NO. : 7,697,658 B2 Page 1 of 1
APPLICATION NO. : 12/362979
DATED : April 13, 2010
INVENTOR(S) : Ge Wang, Yangbo Ye and Hengyong Yu It is certified that error appears in the above-identified patent and that said Letters Patent is hereby corrected as shown below:

At Column 1, Line 17, change grant number EM004287 to read EB004287

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,697,658 B2 Page 1 of 1
APPLICATION NO. : 12/362979
DATED : April 13, 2010
INVENTOR(S) : G. Wang et al.

It is certified that error appears in the above-identified patent and that said Letters Patent is hereby corrected as shown below:

At column 1, line 16, under STATEMENT OF GOVERNMENT INTEREST, replace the entire paragraph with: This invention was made with government support under EB002667, EB004287 and EB007288 awarded by National Institute of Health. The government has certain rights in the invention.

Signed and Sealed this

Seventh Day of December, 2010

David J. Kappos
*Director of the United States Patent and Trademark Office*